(12) United States Patent
Zhong et al.

(10) Patent No.: US 12,268,845 B2
(45) Date of Patent: Apr. 8, 2025

(54) DYNAMIC FORECASTS

(71) Applicant: MEDTRONIC MINIMED, INC., Northridge, CA (US)

(72) Inventors: Yuxiang Zhong, Arcadia, CA (US); Pratik Agrawal, Stevenson Ranch, CA (US); Chantal M. McMahon, Atlanta, GA (US); Huzefa F. Neemuchwala, Simi Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 358 days.

(21) Appl. No.: 17/821,150

(22) Filed: Aug. 19, 2022

(65) Prior Publication Data

US 2023/0009180 A1    Jan. 12, 2023

Related U.S. Application Data

(63) Continuation of application No. 16/137,386, filed on Sep. 20, 2018, now Pat. No. 11,547,799.

(51) Int. Cl.
  *A61M 5/172* (2006.01)
  *G16H 20/17* (2018.01)

(52) U.S. Cl.
  CPC .......... *A61M 5/1723* (2013.01); *G16H 20/17* (2018.01); *A61M 2205/056* (2013.01); *A61M 2205/3303* (2013.01); *A61M 2205/3553* (2013.01); *A61M 2205/3584* (2013.01);
  (Continued)

(58) Field of Classification Search
  None
  See application file for complete search history.

(56) References Cited

U.S. PATENT DOCUMENTS

| | | |
|---|---|---|
| 4,562,751 A | 1/1986 | Nason et al. |
| 4,685,903 A | 8/1987 | Cable et al. |
| 4,755,173 A | 7/1988 | Konopka et al. |

(Continued)

OTHER PUBLICATIONS

Cobelli, et al., "Artificial Pancreas: Past, Present, Future, Diabetes", Nov. 2011, pp. 2672-2682, vol. 60.

(Continued)

*Primary Examiner* — Manuel A Mendez
(74) *Attorney, Agent, or Firm* — Fortem IP LLP

(57) ABSTRACT

Disclosed herein are techniques related to dynamic forecasts. The techniques may involve obtaining, from a medical device, measurement data for a patient; forecasting a plurality of values for a condition of the patient based on a forecasting model and the obtained measurement data; providing a graphical user interface depicting the plurality of forecasted values and comprising a plurality of adjustable graphical user interface elements, each associated with a time period and an activity or event likely to influence the condition; obtaining an adjustment to a first adjustable graphical user interface element; in response to obtaining the adjustment to the first adjustable graphical user interface element, updating at least one of the forecasted values based on the adjustment to the first adjustable graphical user interface element, the obtained measurement data, and the forecasting model; and dynamically updating the graphical user interface to reflect the updated at least one forecasted value.

20 Claims, 17 Drawing Sheets

(52) U.S. Cl.
CPC ... *A61M 2205/505* (2013.01); *A61M 2205/52* (2013.01); *A61M 2230/201* (2013.01)

(56) References Cited

U.S. PATENT DOCUMENTS

| | | | |
|---|---|---|---|
| 5,080,653 A | 1/1992 | Voss et al. |
| 5,097,122 A | 3/1992 | Colman et al. |
| 5,391,250 A | 2/1995 | Cheney et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Vanantwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode et al. |
| 8,202,250 B2 | 6/2012 | Stutz |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente et al. |
| 8,674,288 B2 | 3/2014 | Hanson et al. |
| 8,818,782 B2 | 8/2014 | Thukral et al. |
| 9,419,704 B2 | 8/2016 | Galley et al. |
| 9,465,917 B2 | 10/2016 | Soni et al. |
| 2004/0122484 A1* | 6/2004 | Hatlestad ............... G16H 15/00 607/60 |
| 2005/0065760 A1 | 3/2005 | Murtfeldt et al. |
| 2006/0031094 A1 | 2/2006 | Van et al. |
| 2007/0123819 A1 | 5/2007 | Mernoe et al. |
| 2008/0183060 A1 | 7/2008 | Steil et al. |
| 2010/0160861 A1 | 6/2010 | Causey et al. |
| 2013/0338630 A1 | 12/2013 | Agrawal et al. |
| 2014/0066889 A1 | 3/2014 | Grosman et al. |
| 2014/0142535 A1 | 5/2014 | Imhof et al. |
| 2014/0200559 A1 | 7/2014 | Doyle et al. |
| 2014/0276554 A1 | 9/2014 | Finan et al. |
| 2015/0254724 A1 | 9/2015 | Kusukame et al. |
| 2017/0091419 A1 | 3/2017 | Hoglund et al. |
| 2017/0220751 A1 | 8/2017 | Davis et al. |
| 2018/0039757 A1 | 2/2018 | Sudharsan |
| 2018/0043095 A1 | 2/2018 | Finan et al. |
| 2018/0169333 A1 | 6/2018 | Grosman et al. |
| 2020/0093988 A1 | 3/2020 | Zhong et al. |
| 2020/0098464 A1 | 3/2020 | Velado et al. |

OTHER PUBLICATIONS

Grosman, "Multi-Zone-MPC: Clinical Inspired Control Algorithm for the Artificial Pancreas", Preprints of the 18th IFAC World Congress, Milano, Italy, Aug. 28, 2011, pp. 7120-7125.

Palma, et al., "A Multi-Model Structure for Model Predictive Control", Annual Reviews in Control, Oct. 20, 2003, pp. 47-52, vol. 28.

* cited by examiner

DYNAMIC FORECASTS

CROSS-REFERENCE TO RELATED APPLICATIONS

This application is a continuation of U.S. application Ser. No. 16/137,386, filed Sep. 20, 2018, now U.S. Pat. No. 11,547,799, which is incorporated herein by reference in its entirety.

TECHNICAL FIELD

Embodiments disclosed herein relate generally to the medical arts and more particularly to dynamic forecasts.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. Regulating blood glucose level is complicated by variations in the response time for the type of insulin being used along with each user's individual insulin response. Furthermore, a user's daily activities and experiences may cause that user's insulin response to vary throughout the course of a day or from one day to the next. Thus, it is desirable to account for the anticipated variations or fluctuations in the user's insulin response caused by the user's activities or other condition(s) experienced by the user.

Managing a diabetic's blood glucose level is also complicated by the user's consumption of meals or carbohydrates. Often, a user manually administers a bolus of insulin at or around meal time to mitigate postprandial hyperglycemia. To effectively mitigate postprandial hyperglycemia while also avoiding postprandial hypoglycemia, the user is often required to estimate the amount of carbohydrates being consumed, with that amount of carbohydrates then being utilized to determine the appropriate bolus dosage. While undesirably increasing the burden on the patient for managing his or her therapy, manual errors such as miscounting carbohydrates or failing to initiate a bolus in a timely manner can also reduce the therapy effectiveness. Accordingly, there is a need facilitate improved glucose control that reduces patient workload.

BRIEF SUMMARY

Disclosed herein are techniques related to dynamic forecasts. The techniques may be practiced using a processor-implemented method; a system comprising one or more processors and one or more processor-readable media; and/or one or more non-transitory processor-readable media.

In some embodiments, the techniques may involve obtaining, from a medical device, measurement data for a patient. The techniques may further involve forecasting a plurality of values for a condition of the patient based on a forecasting model associated with the patient and the obtained measurement data for the patient; providing, for display on a portable electronic device, a graphical user interface depicting the plurality of forecasted values and comprising a plurality of adjustable graphical user interface elements, each adjustable graphical user interface element being associated with a time period and an activity or event likely to influence the condition of the patient; obtaining, via the graphical user interface, an adjustment to a first adjustable graphical user interface element of the graphical user interface; in response to obtaining the adjustment to the first adjustable graphical user interface element, updating at least one of the forecasted values for the condition of the patient based on the adjustment to the first adjustable graphical user interface element, the obtained measurement data, and the forecasting model associated with the patient; and dynamically updating the graphical user interface to reflect the updated at least one forecasted value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
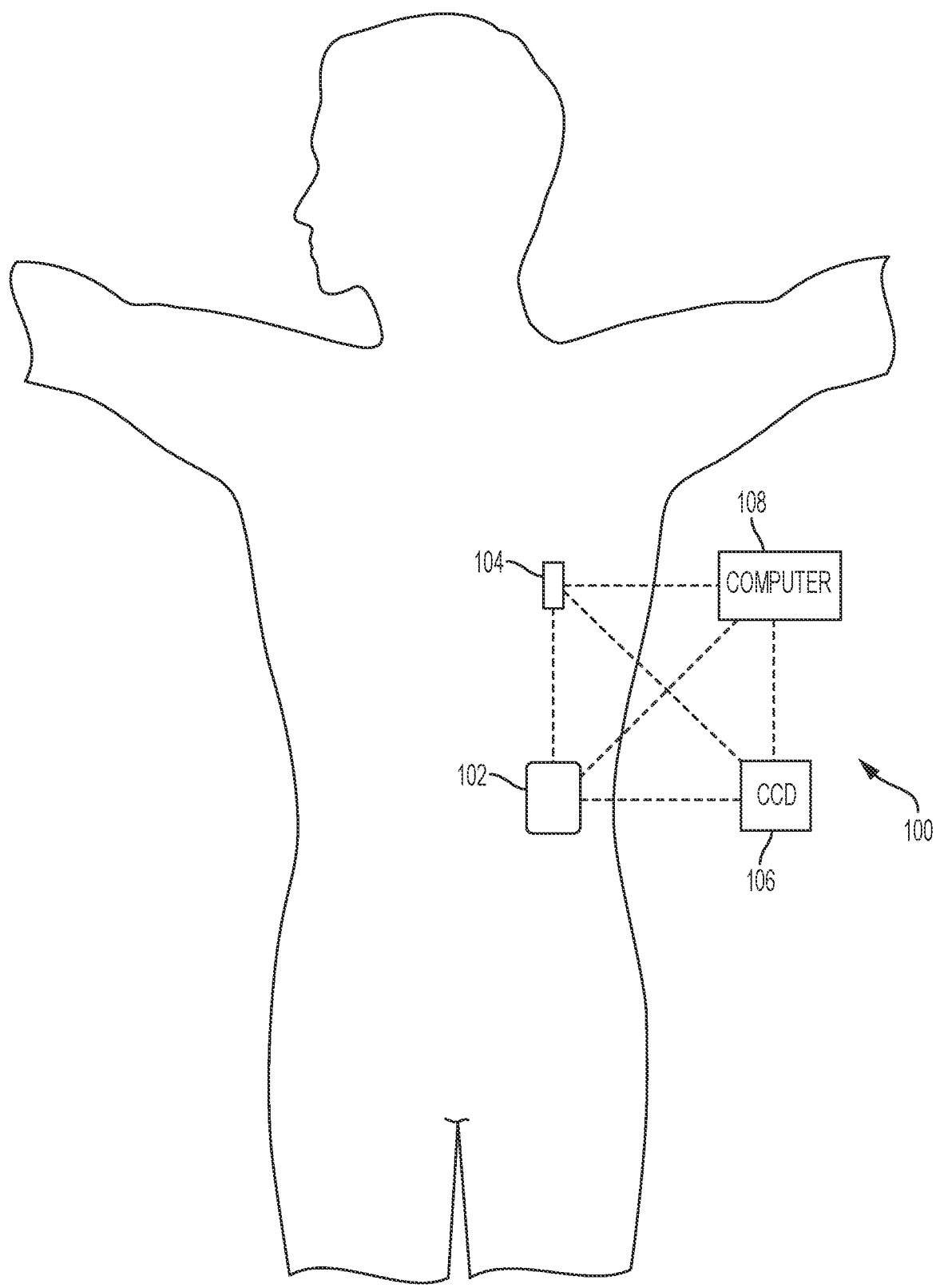
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device, exemplary embodiments described below may be primarily implemented in the form of medical devices, such as portable electronic medical devices. Although many different applications are possible, the following description may focus on a fluid infusion device (or infusion pump) as part of an infusion system deployment. That said, the subject matter may be implemented in an equivalent manner in the context of other medical devices, such as continuous glucose monitoring (CGM) devices, smart injection pens, and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor or other actuation arrangement that is operable to displace a plunger (or stopper) of a reservoir provided within the fluid infusion device to deliver a dosage of fluid, such as insulin, to the body of a user. In one or more exemplary embodiments, delivery commands (or dosage commands) that govern operation of the motor are determined based on a difference between a measured value for a physiological condition in the body of the user and a target value using closed-loop control to regulate the measured value to the target value.

As described in greater detail below in the context of FIGS. 9-12, in one or more exemplary embodiments, a planning graphical user interface (GUI) display is provided that depicts forecasted values for a patient's physiological condition at different times in the future. For example, as described in greater detail in U.S. patent application Ser. No. 15/933,264, which is hereby incorporated by reference, a patient's glucose level may be forecasted on an hourly basis or for discrete time intervals in the future using a patient-specific forecasting model. Additionally, the occurrence of future insulin deliveries, future meals, future exercise events, and/or future medication dosages and likely attributes or characteristics associated therewith may be predicted or otherwise determined within the forecast horizon of the planning GUI display based on historical data associated with the patient, as described in U.S. patent application Ser. No. 15/847,750, which is incorporated by reference herein. The predicted patient behaviors or activities likely to influence the patient's glucose level and the relative timing and attributes of those behaviors or activities may be input or otherwise provided to patient-specific forecasting model, which, in turn, generates or otherwise outputs hourly forecast glucose values for the patient. The planning GUI display includes graphical representations of the hourly forecast glucose values with respect to time along with graphical indicia of the predicted patient behaviors or activities and their associated attributes or characteristics at their predicted times within the forecast window (or horizon).

In exemplary embodiments, the planning GUI display includes GUI elements that are manipulable, adjustable, or otherwise configurable by the patient or another user to adjust or modify attributes of the predicted patient behaviors or activities, delete or otherwise remove predicted patient behaviors or activities at particular times within the forecast horizon, and/or add anticipated patient behaviors or activities and corresponding attributes at different times within the forecast horizon. For example, a user may adjust the intensity or duration of an anticipated exercise event, increase or decrease the amount of carbs for an anticipated meal in the future, add an insulin bolus at a particular time of day, and/or the like. In response to a user adjustment to a GUI element on the planning GUI display, the hourly forecast glucose values depicted on the planning GUI display are dynamically updated to reflect the likely result of the adjustment, for example, by modifying the attribute values for an anticipated event that are input to the patient's forecasting model at the anticipated time associated with the event. In this regard, the patient or other user may view how potential activities or behaviors in the future are likely to influence the patient's forecasted glucose levels, and thereby plan the patient's daily activities to achieve a desired outcome for the patient. For example, the patient or other user may utilize the GUI elements to adjust or otherwise tune the patient's daily activities to maintain the patient's forecasted glucose levels within a desired target range, below an upper threshold value, above a lower threshold value, substantially equal to a target value, and/or the like.

In one or more embodiments, the planning GUI display includes a GUI element that allows the patient or other user to confirm, save, or otherwise set the preplanned activities and events for the patient as a reference plan utilize to generate alerts, reminders, or other notifications for the patient during the time period associated with the plan. For example, upon reaching a time associated with a planned activity or event, a reminder may be automatically generated that reminds the patient to engage in the planned activity or event with the planned attributes or characteristics to maintain his or her glucose level in line with the preplanned trajectory or forecast glucose values for subsequent times of day. Additionally, when the patient's current or real-time glucose level at a particular time of day deviates from the originally forecasted glucose value at that time of day, a notification or alert may be provided to the patient that notifies the patient so that the patient may engage in one or more remedial actions to alter his or her glucose levels in a manner that reduces or otherwise minimizes the deviation from the patient's originally forecasted glucose values or trajectory thereof going forward.

As described in greater detail below in the context of FIG. 13, the state or operational context associated with the patient at a particular time of day may be utilized to generate or otherwise provide recommendations for activities or events for a patient to engage in along with corresponding recommended attributes or characteristics associated therewith to achieve a desired outcome for the patient's glucose level. For example, in connection with the planning GUI display, based on predicted meal or exercise events at different times of day within the forecast window, a recommended insulin bolus amount at a particular time of day within the forecast window may be determined that is likely to achieve a desired glucose outcome (e.g., a patient glucose level within a desired target range). The planning GUI display may be initially populated with the recommended insulin bolus amount at the corresponding time of day, thereby allowing the patient or other user to assess, modify, and/or delete the recommended bolus amount from his or her activity plan. Subsequently, the current real-time state or operational context associated with the patient during the day may be utilized to identify or otherwise determine recommended activities for guiding the patient's glucose levels back towards the originally planned and forecasted glucose values (or trajectory thereof).

In exemplary embodiments, the state or operational context associated with the patient at the particular time for which the recommendation is to be generated is utilized to identify a cluster of historical patient states or operational contexts (which may be for the same patient or from different patients) that are substantially similar to the state or operational context for the recommendation. Machine learning may be utilized to determine an equation, function, or model for calculating the glucose level as a function of a subset of input variables that are correlative to or predictive of the subsequent glucose level based on the historical data associated with the cluster of historical patient states. Thereafter, using the state or operational context associated with the patient at the particular time, one or more attributes for activities or events (e.g., a bolus amount of insulin, an amount of carbohydrates consumed, an exercise duration and/or intensity, and/or the like) that are input to the glucose prediction model may be varied to determine a range of potential predicted glucose outcomes for the patient given the patient's current state or operational context at the time of the recommendation. The subset of input variables that provide a predicted glucose outcome that is equal to or otherwise within a desired range of values may then be analyzed to identify or otherwise determine a recommended activity for the patient to engage in and a recommended attribute associated therewith. For example, a median or mean bolus amount of insulin may be identified from among the range of potential bolus amounts that are likely to achieve a predicted glucose outcome within a threshold amount of an originally forecast glucose level according to the patient's activity plan, and that median or mean bolus amount of insulin may be recommended to the patient to guide the patient's glucose level back towards the originally planned and forecasted glucose values (or trajectory thereof).

As described in greater detail below in the context of FIG. 14, in accordance with one or more embodiments, the current environmental context associated with the patient is utilized to adjust or otherwise influence recommendations based on the patient's current environment. In this regard, in some embodiments, the current geographic location and/or the current meteorological conditions may be utilized as an input to the recommendation model, or the current geographic location and/or the current meteorological conditions may be utilized to adjust the relative weightings assigned to inputs to the recommendation model. In yet other embodiments, the current geographic location and/or the current meteorological conditions may be utilized to adjust the relative rankings or weightings assigned to outputs of the recommendation model(s). For example, if it is less likely that a patient will engage in the recommended activity (or the recommended amount thereof) given the current meteorological conditions (e.g., a recommended amount of exercise when it is raining, humid, hot, etc.), the recommendation process may alter the recommendation to instead recommend an activity that the patient is more likely to engage in given the current meteorological conditions. In this regard, when the recommendation model is capable of multidimensional recommendations across multiple potential different activities or variables (e.g., carbohydrate consumption, insulin bolusing, exercise, etc.), a different combination of activities may be recommended based on the current geographic location and/or the current meteorological conditions. Additionally, the current geographic location may be utilized to provide more detailed recommendations to the patient, for example, by identifying nearby businesses or services that may be utilized to achieve or perform the recommended activity (e.g., nearby restaurants, grocery stores, fitness centers, recreation areas, etc.).

Infusion System Overview

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589, 229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
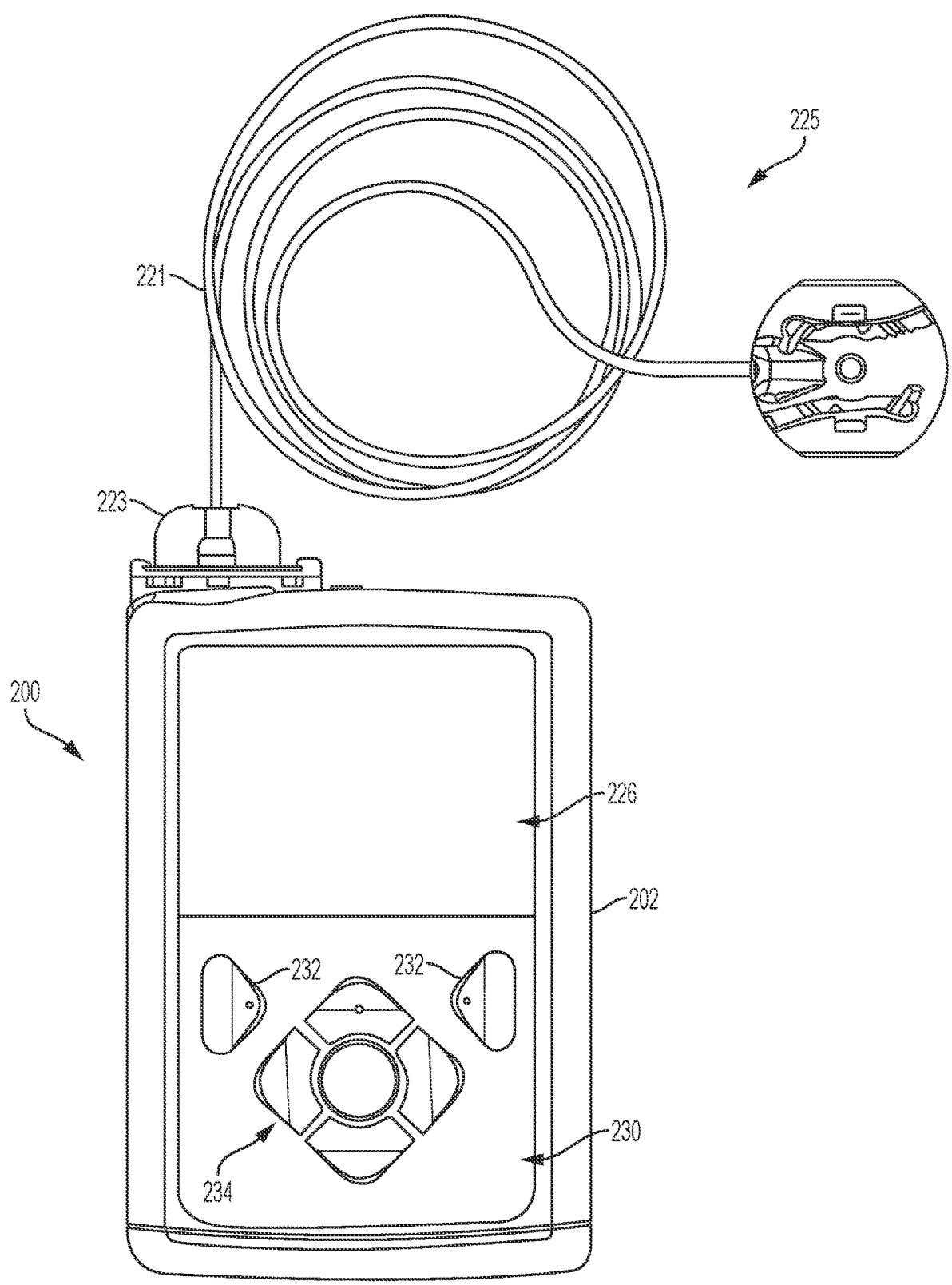
FIG. 2 depicts a plan view of an exemplary embodiment of a fluid infusion device suitable for use in the infusion system of FIG. 1.
Figure 3:
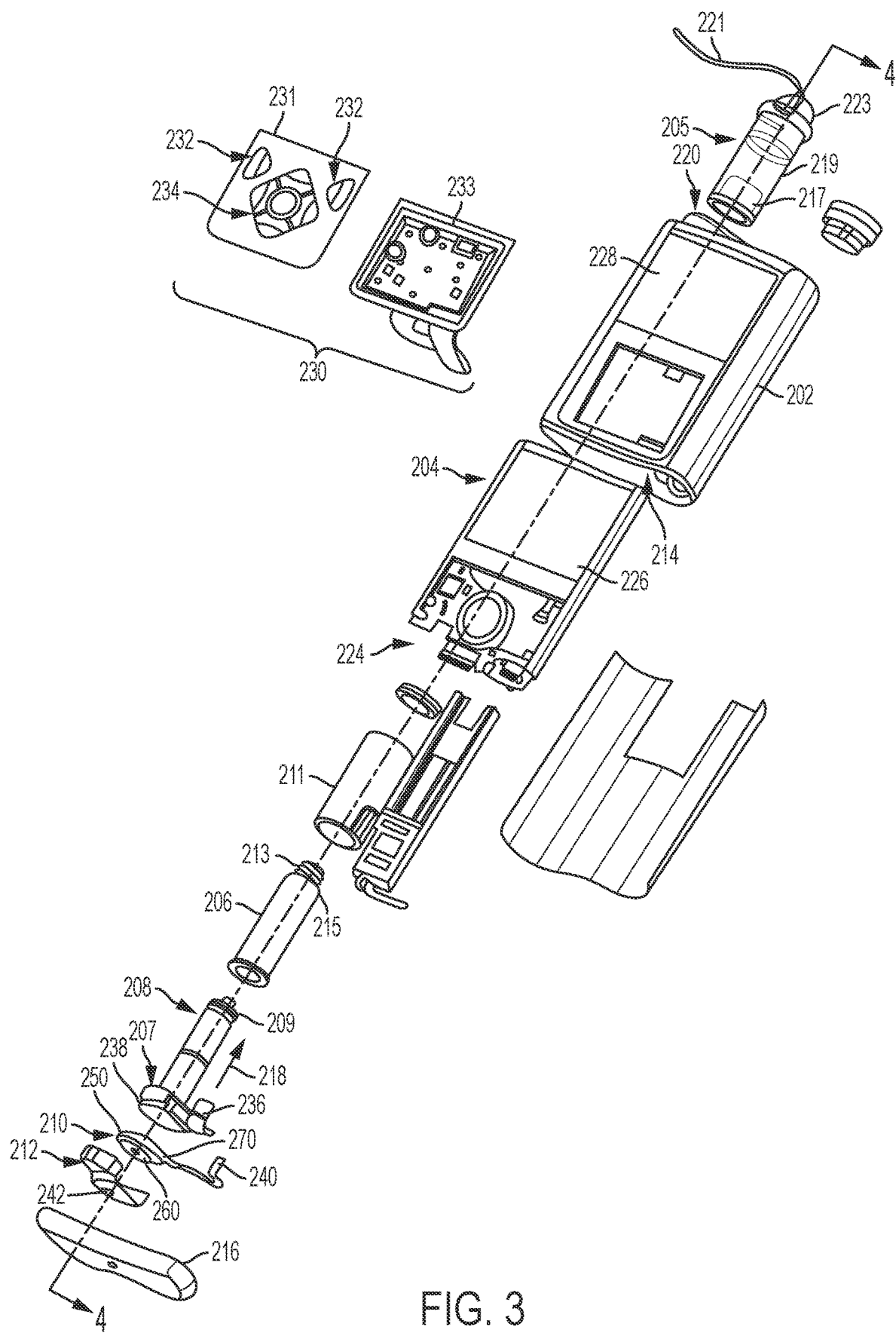
FIG. 3 is an exploded perspective view of the fluid infusion device of FIG. 2.
Figure 4:
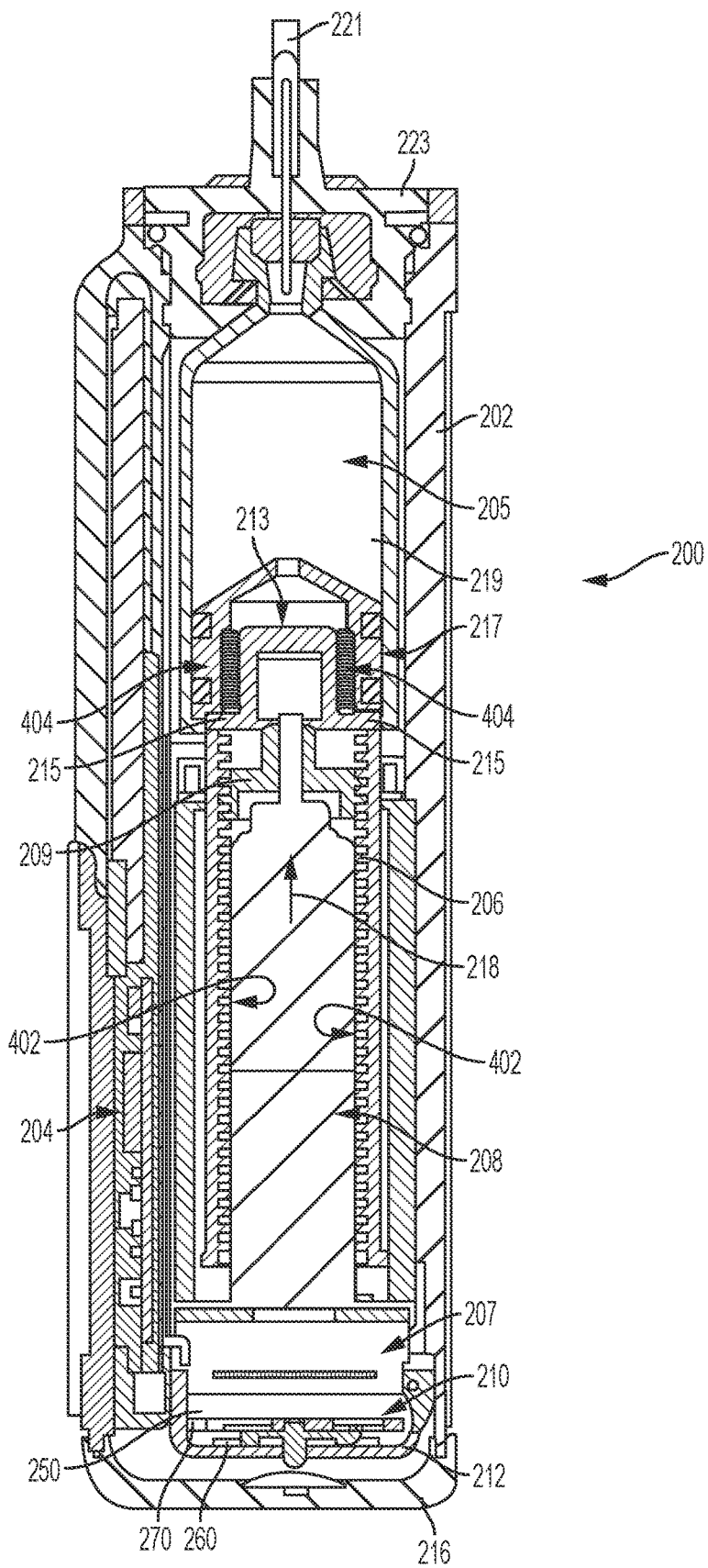
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user.

The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
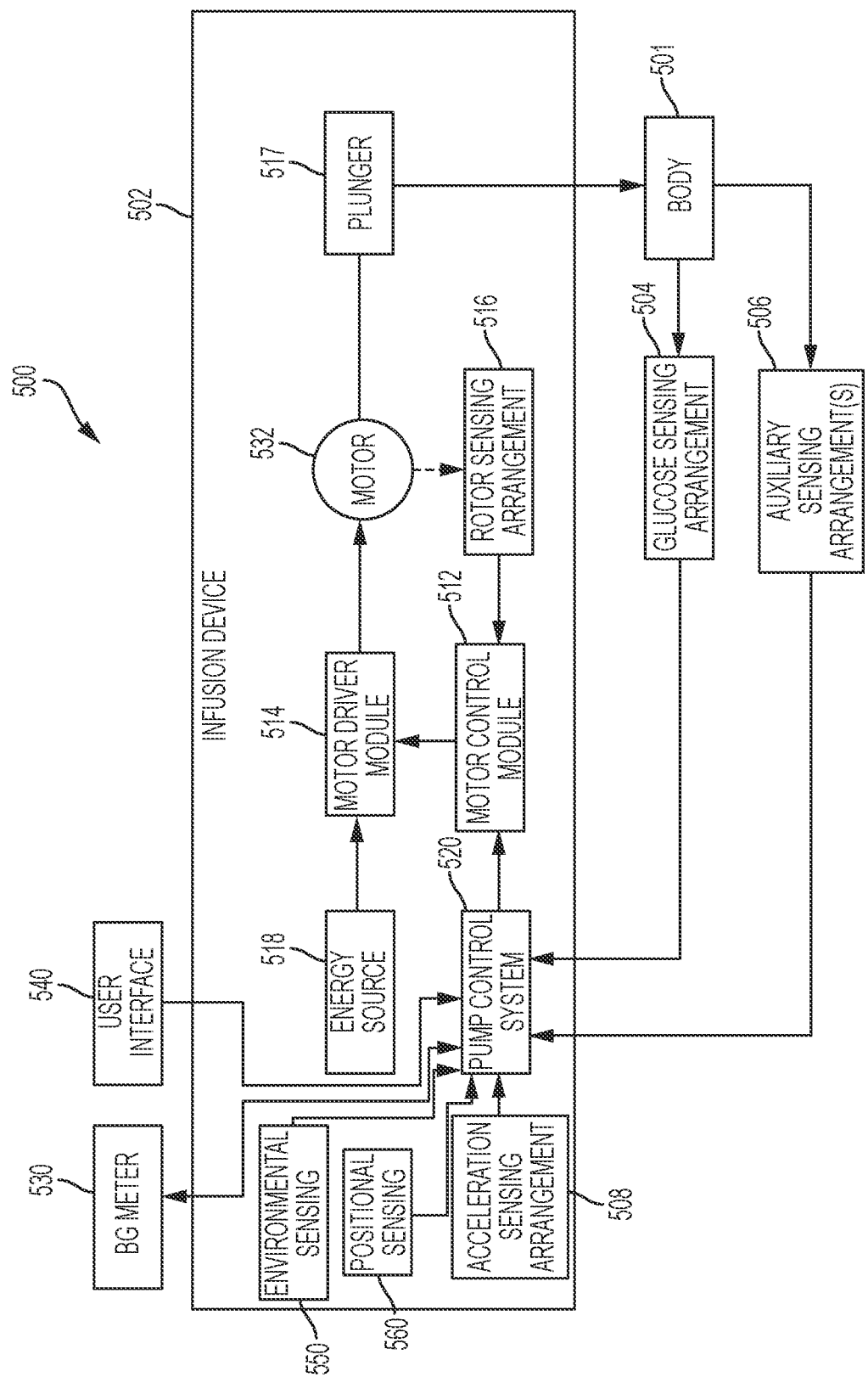
FIG. 5 is a block diagram of an exemplary infusion system suitable for use with a fluid infusion device in one or more embodiments.

FIG. 5 depicts an exemplary embodiment of an infusion system 500 suitable for use with an infusion device 502, such as any one of the infusion devices 102, 200 described above. The infusion system 500 is capable of controlling or otherwise regulating a physiological condition in the body 501 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., sensing arrangement 504) communicatively coupled to the infusion device 502. However, it should be noted that in alternative embodiments, the condition being regulated by the infusion system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the infusion system 500.

In exemplary embodiments, the sensing arrangement 504 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In exemplary embodiments, the infusion system 500 also includes one or more additional sensing arrangements 506, 508 configured to sense, detect, measure or otherwise quantify a characteristic of the body 501 of the user that is indicative of a condition in the body 501 of the user. In this regard, in addition to the glucose sensing arrangement 504, one or more auxiliary sensing arrangements 506 may be worn, carried, or otherwise associated with the body 501 of the user to measure characteristics or conditions of the user (or the user's activity) that may influence the user's glucose levels or insulin sensitivity. For example, a heart rate sensing arrangement 506 could be worn on or otherwise associated with the user's body 501 to sense, detect, measure or otherwise quantify the user's heart rate, which, in turn, may be indicative of exercise (and the intensity thereof) that is likely to influence the user's glucose levels or insulin response in the body 501. In yet another embodiment, another invasive, interstitial, or subcutaneous sensing arrangement 506 may be inserted into the body 501 of the user to obtain measurements of another physiological condition that may be indicative of exercise (and the intensity thereof), such as, for example, a lactate sensor, a ketone sensor, or the like. Depending on the embodiment, the auxiliary sensing arrangement(s) 506 could be realized as a standalone component worn by the user, or alternatively, the auxiliary sensing arrangement(s) 506 may be integrated with the infusion device 502 or the glucose sensing arrangement 504.

The illustrated infusion system 500 also includes an acceleration sensing arrangement 508 (or accelerometer) that may be worn on or otherwise associated with the user's body 501 to sense, detect, measure or otherwise quantify an acceleration of the user's body 501, which, in turn, may be indicative of exercise or some other condition in the body 501 that is likely to influence the user's insulin response. While the acceleration sensing arrangement 508 is depicted as being integrated into the infusion device 502 in FIG. 5, in alternative embodiments, the acceleration sensing arrangement 508 may be integrated with another sensing arrangement 504, 506 on the body 501 of the user, or the acceleration sensing arrangement 508 may be realized as a separate standalone component that is worn by the user.

In one or more exemplary embodiments, the infusion device 502 also includes one or more environmental sensing arrangements 550 to sense, detect, measure or otherwise quantify the current operating environment around the infusion device 502. In this regard, the environmental sensing arrangements 550 may include one or more of a temperature sensing arrangement (or thermometer), a humidity sensing arrangement, a pressure sensing arrangement (or barometer), and/or the like. In exemplary embodiments, the infusion device 502 also includes a position sensing arrangement 560 to sense, detect, measure or otherwise quantify the current geographic location of the infusion device 502, such as, for example, a global positioning system (GPS) receiver. Again, it should be noted that while the sensing arrangement 550, 560 are depicted as being integrated into the infusion device 502 in FIG. 5, in alternative embodiments, one or more of the sensing arrangements 550, 560 may be integrated with another sensing arrangement 504, 506 on the body 501 of the user, or one or more of the sensing arrangements 550, 560 may be realized as a separate standalone component that is worn by the user.

In the illustrated embodiment, the pump control system 520 generally represents the electronics and other components of the infusion device 502 that control operation of the fluid infusion device 502 according to a desired infusion delivery program in a manner that is influenced by the sensed glucose value indicating the current glucose level in the body 501 of the user. For example, to support a closed-loop operating mode, the pump control system 520 maintains, receives, or otherwise obtains a target or commanded glucose value, and automatically generates or otherwise determines dosage commands for operating an actuation arrangement, such as a motor 532, to displace the plunger 517 and deliver insulin to the body 501 of the user based on the difference between the sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit (s), insulin delivery limit(s), and/or other glucose threshold value(s) in a data storage element accessible to the pump control system 520.

Still referring to FIG. 5, the target glucose value and other threshold glucose values utilized by the pump control system 520 may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 532 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid, such as insulin, that is capable of influencing the user's physiological condition to the body 501 of the user via a fluid delivery path (e.g., via tubing 221 of an infusion set 225). A motor driver module 514 is coupled between an energy source 518 and the motor 532. The motor control module 512 is coupled to the motor driver module 514, and the motor control module 512 generates or otherwise provides command signals that operate the motor driver module 514 to provide current (or power) from the energy source 518 to the motor 532 to displace the plunger 517 in response to receiving, from a pump control system 520, a dosage command indicative of the desired amount of fluid to be delivered.

In exemplary embodiments, the energy source 518 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 518 into alternating electrical signals applied to respective phases of the stator windings of the motor 532 that result in current flowing through the stator windings that generates a stator magnetic field and causes the rotor of the motor 532 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 532 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 532 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 532 to achieve the desired delivery of fluid to the user.

When the motor control module 512 is operating the motor driver module 514, current flows from the energy source 518 through the stator windings of the motor 532 to produce a stator magnetic field that interacts with the rotor magnetic field. In some embodiments, after the motor control module 512 operates the motor driver module 514 and/or motor 532 to achieve the commanded dosage, the motor control module 512 ceases operating the motor driver module 514 and/or motor 532 until a subsequent dosage command is received. In this regard, the motor driver module 514 and the motor 532 enter an idle state during which the motor driver module 514 effectively disconnects or isolates the stator windings of the motor 532 from the energy source 518. In other words, current does not flow from the energy source 518 through the stator windings of the motor 532 when the motor 532 is idle, and thus, the motor 532 does not consume power from the energy source 518 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 502, while in alternative embodiments, the pump control system 520 may be implemented by a remote computing device that is physically distinct and/or separate from the infusion device 502, such as, for example, the CCD 106 or the computing device 108.

Figure 6:
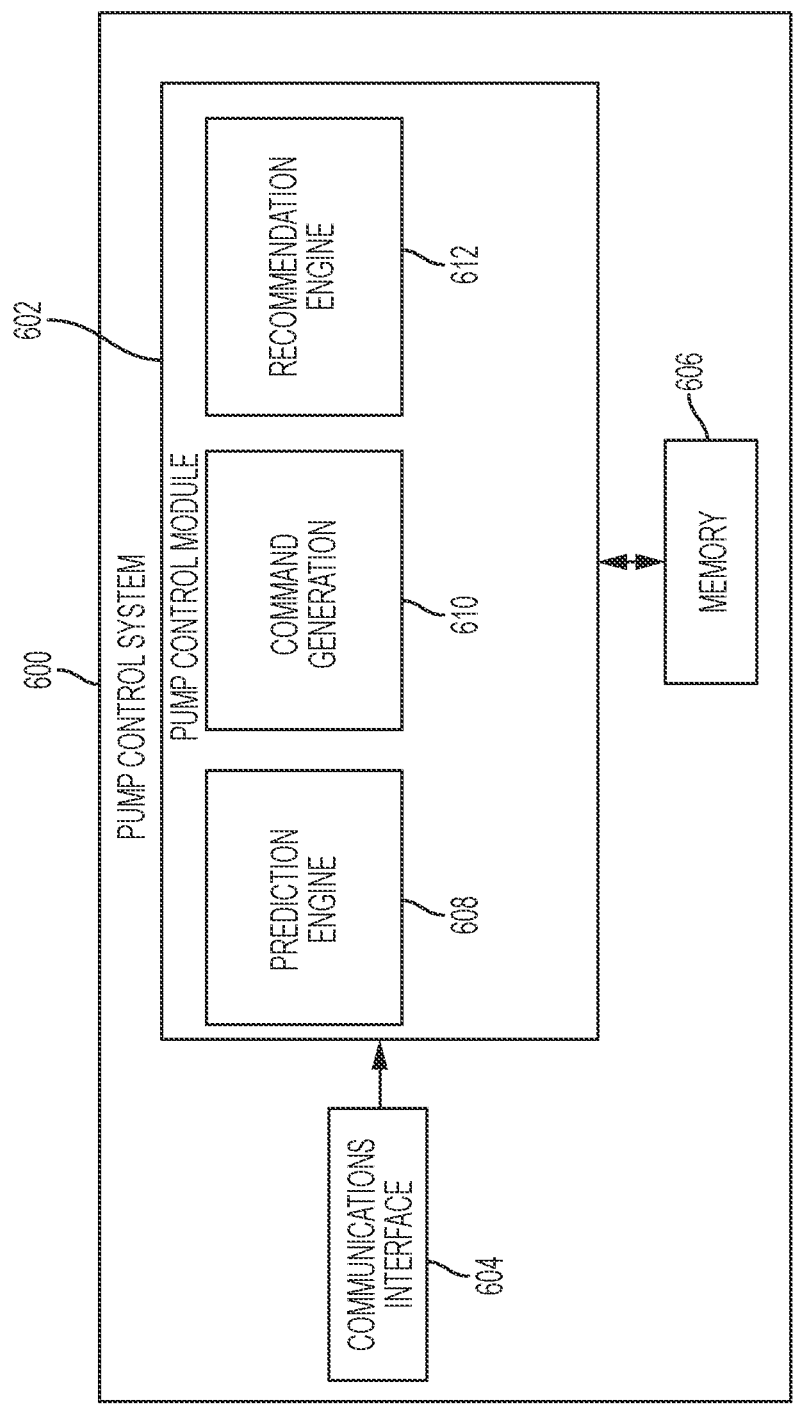
FIG. 6 is a block diagram of an exemplary pump control system suitable for use in the infusion device in the infusion system of FIG. 5 in one or more embodiments.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In various embodiments, the pump control module 602 is also coupled to one or more user interface elements (e.g., user interface 540) for receiving user inputs (e.g., target glucose values or other glucose thresholds) and providing notifications, alerts, or other therapy information to the user.

The communications interface 604 generally represents the hardware, circuitry, logic, firmware and/or other components of the pump control system 600 that are coupled to the pump control module 602 and configured to support communications between the pump control system 600 and one or more of the various sensing arrangements 504, 506, 508, 550, 560. In this regard, the communications interface 604 may include or otherwise be coupled to one or more transceiver modules capable of supporting wireless communications between the pump control system 520, 600 and an external sensing arrangement 504, 506. For example, the communications interface 604 may be utilized to wirelessly receive sensor measurement values or other measurement data from each external sensing arrangement 504, 506 in an infusion system 500. In other embodiments, the communications interface 604 may be configured to support wired communications to/from the external sensing arrangement(s) 504, 506. In various embodiments, the communications interface 604 may also support communications with a remote server or another electronic device in an infusion system (e.g., to upload sensor measurement values, receive control information, and the like).

The pump control module 602 generally represents the hardware, circuitry, logic, firmware and/or other component of the pump control system 600 that is coupled to the communications interface 604 and the sensing arrangements 504, 506, 508, 550, 560 and configured to determine dosage commands for operating the motor 532 to deliver fluid to the body 501 based on measurement data received from the sensing arrangements 504, 506, 508, 550, 560 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 532 of the infusion device 502 in an autonomous operating mode based at least in part on a current measurement value for a condition in the body 501 of the user. For example, in a closed-loop operating mode, the command generation application 610 may determine a dosage command for operating the motor 532 to deliver insulin to the body 501 of the user based at least in part on the current glucose measurement value most recently received from the sensing arrangement 504 to regulate the user's blood glucose level to a target reference glucose value. In various embodiments, the dosage commands may also be adjusted or otherwise influenced by contextual measurement data, that is, measurement data that characterizes, quantifies, or otherwise indicates the contemporaneous or concurrent operating context for the dosage command(s), such as, for example, environmental measurement data obtained from an environmental sensing arrangement 550, the current location information obtained from a GPS receiver 560 and/or other contextual information characterizing the current operating environment for the infusion device 502. Additionally, the command generation application 610 may generate dosage commands for boluses that are manually-initiated or otherwise instructed by a user via a user interface element.

In one or more exemplary embodiments, the pump control module 602 also implements or otherwise executes a prediction application 608 (or prediction engine) that is configured to estimate or otherwise predict the future physiological condition and potentially other future activities, events, operating contexts, and/or the like in a personalized, patient-specific (or patient-specific) manner. In this regard, in some embodiments, the prediction engine 608 cooperatively configured to interact with the command generation application 610 to support adjusting dosage commands or control information dictating the manner in which dosage commands are generated in a predictive or prospective manner. In this regard, in some embodiments, based on correlations between current or recent measurement data and the current operational context relative to historical data associated with the patient, the prediction engine 608 may forecast or otherwise predict future glucose levels of the patient at different times in the future, and correspondingly adjust or otherwise modify values for one or more parameters utilized by the command generation application 610 when determining dosage commands in a manner that accounts for the predicted glucose level, for example, by modifying a parameter value at a register or location in memory 606 referenced by the command generation application 610. In various embodiments, the prediction engine 608 may predict meals or other events or activities that are likely to be engaged in by the patient and output or otherwise provide an indication of how the patient's predicted glucose level is likely to be influenced by the predicted events, which, in turn, may then be reviewed or considered by the patient to prospectively adjust his or her behavior and/or utilized to adjust the manner in which dosage commands are generated to regulate glucose in a manner that accounts for the patient's behavior in a personalized manner. In one or more exemplary embodiments, the pump control module 602 also implements or otherwise executes a recommendation application 612 (or recommendation engine) that is configured to support providing recommendations to the patient, as described in greater detail below.

Still referring to FIG. 6, depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the applications 608, 610, 612 and perform tasks, operations, functions, and processes described herein.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
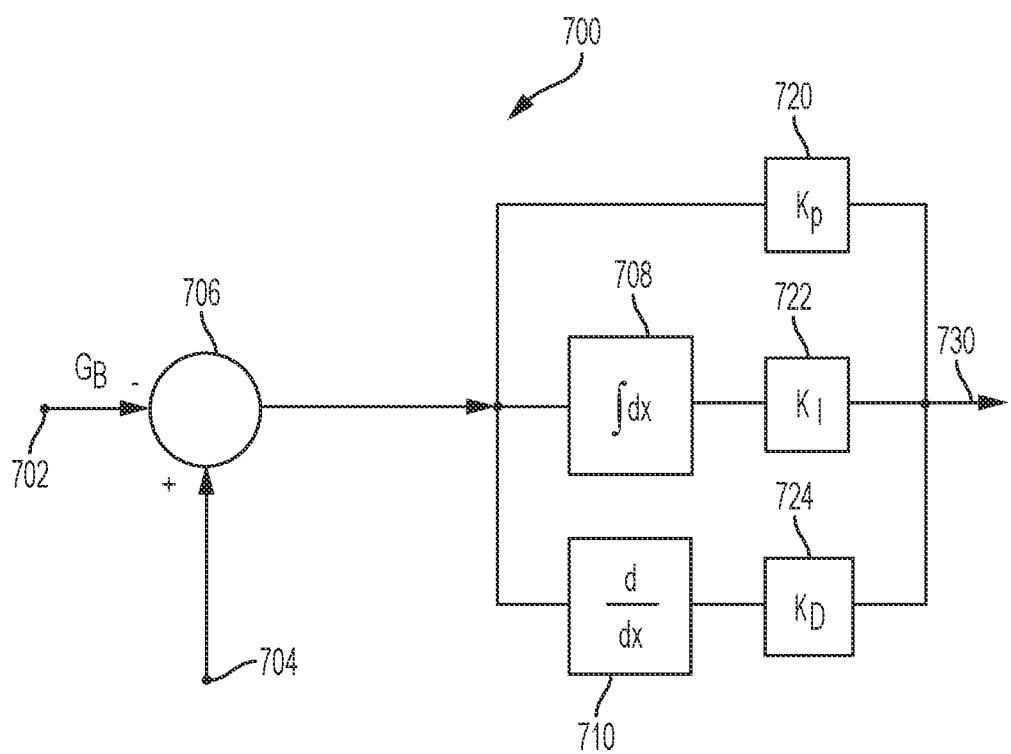
FIG. 7 is a block diagram of a closed-loop control system that may be implemented or otherwise supported by the pump control system in the fluid infusion device of FIGS. 5-6 in one or more exemplary embodiments.

FIG. 7 depicts an exemplary closed-loop control system 700 that may be implemented by a pump control system 520, 600 to provide a closed-loop operating mode that autonomously regulates a condition in the body of a user to a reference (or target) value. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 532 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 532 to deliver insulin to the body of the user to influence the user's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, Kr, to obtain the integral term. The derivative term path includes a derivative block 710 that determines the derivative of the difference and a gain block 724 that multiplies the derivative of the difference by a derivative gain coefficient, KD, to obtain the derivative term. The proportional term, the integral term, and the derivative term are then added or otherwise combined to obtain a delivery command that is utilized to operate the motor at output 730. Various implementation details pertaining to closed-loop PID control and determining gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

Figure 8:
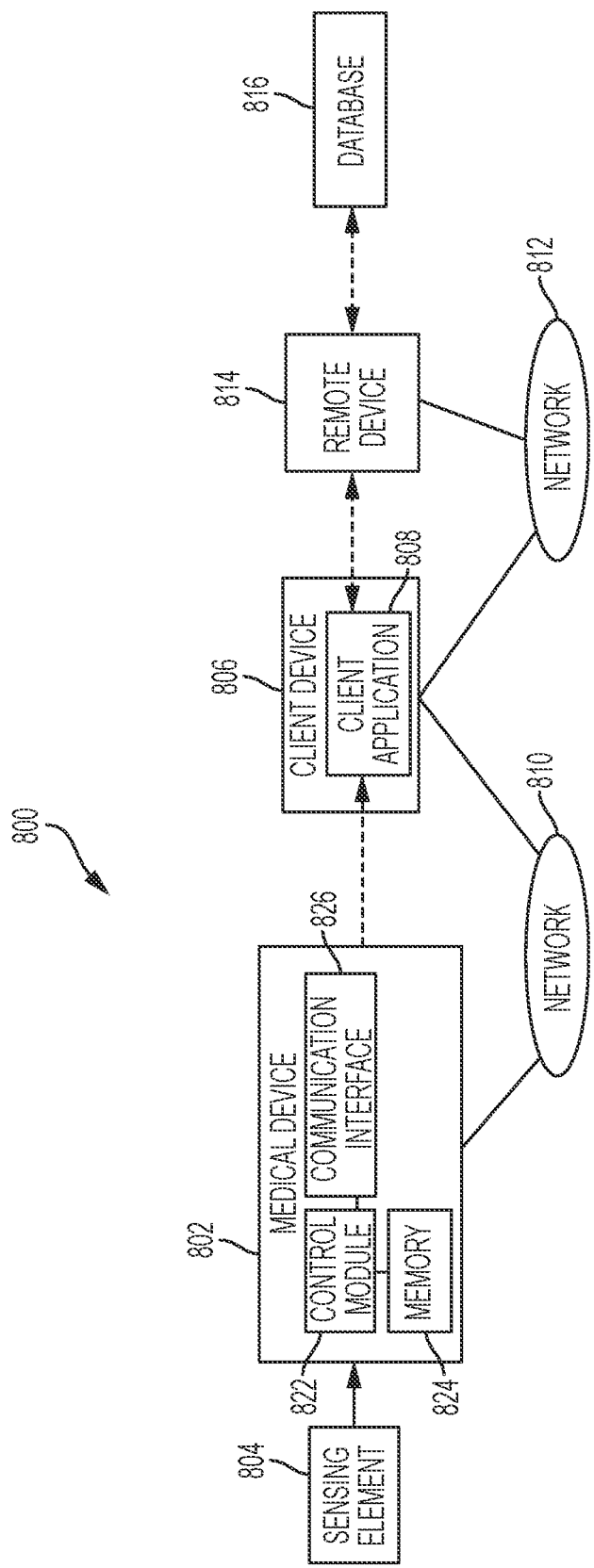
FIG. 8 is a block diagram of an exemplary patient monitoring system.

FIG. 8 depicts an exemplary embodiment of a patient monitoring system 800. The patient monitoring system 800 includes a medical device 802 that is communicatively coupled to a sensing element 804 that is inserted into the body of a patient or otherwise worn by the patient to obtain measurement data indicative of a physiological condition in the body of the patient, such as a sensed glucose level. The medical device 802 is communicatively coupled to a client device 806 via a communications network 810, with the client device 806 being communicatively coupled to a remote device 814 via another communications network 812. In this regard, the client device 806 may function as an intermediary for uploading or otherwise providing measurement data from the medical device 802 to the remote device 814. It should be appreciated that FIG. 8 depicts a simplified representation of a patient monitoring system 800 for purposes of explanation and is not intended to limit the subject matter described herein in any way.

In exemplary embodiments, the client device 806 is realized as a mobile phone, a smartphone, a tablet computer, or other similar mobile electronic device; however, in other embodiments, the client device 806 may be realized as any sort of electronic device capable of communicating with the medical device 802 via network 810, such as a laptop or notebook computer, a desktop computer, or the like. In exemplary embodiments, the network 810 is realized as a Bluetooth network, a ZigBee network, or another suitable personal area network. That said, in other embodiments, the network 810 could be realized as a wireless ad hoc network, a wireless local area network (WLAN), or local area network (LAN). The client device 806 includes or is coupled to a display device, such as a monitor, screen, or another conventional electronic display, capable of graphically presenting data and/or information pertaining to the physiological condition of the patient. The client device 806 also includes or is otherwise associated with a user input device, such as a keyboard, a mouse, a touchscreen, or the like, capable of receiving input data and/or other information from the user of the client device 806.

In exemplary embodiments, a user, such as the patient, the patient's doctor or another healthcare provider, or the like, manipulates the client device 806 to execute a client application 808 that supports communicating with the medical device 802 via the network 810. In this regard, the client application 808 supports establishing a communications session with the medical device 802 on the network 810 and receiving data and/or information from the medical device 802 via the communications session. The medical device 802 may similarly execute or otherwise implement a corresponding application or process that supports establishing the communications session with the client application 808. The client application 808 generally represents a software module or another feature that is generated or otherwise implemented by the client device 806 to support the processes described herein. Accordingly, the client device 806 generally includes a processing system and a data storage element (or memory) capable of storing programming instructions for execution by the processing system, that, when read and executed, cause processing system to create, generate, or otherwise facilitate the client application 808 and perform or otherwise support the processes, tasks, operations, and/or functions described herein. Depending on the embodiment, the processing system may be implemented using any suitable processing system and/or device, such as, for example, one or more processors, central processing units (CPUs), controllers, microprocessors, microcontrollers, processing cores and/or other hardware computing resources configured to support the operation of the processing system described herein. Similarly, the data storage element or memory may be realized as a random access memory (RAM), read only memory (ROM), flash memory, magnetic or optical mass storage, or any other suitable non-transitory short or long term data storage or other computer-readable media, and/or any suitable combination thereof.

In one or more embodiments, the client device 806 and the medical device 802 establish an association (or pairing) with one another over the network 810 to support subsequently establishing a point-to-point or peer-to-peer communications session between the medical device 802 and the client device 806 via the network 810. For example, in accordance with one embodiment, the network 810 is realized as a Bluetooth network, wherein the medical device 802 and the client device 806 are paired with one another (e.g., by obtaining and storing network identification information for one another) by performing a discovery procedure or another suitable pairing procedure. The pairing information obtained during the discovery procedure allows either of the medical device 802 or the client device 806 to initiate the establishment of a secure communications session via the network 810.

In one or more exemplary embodiments, the client application 808 is also configured to store or otherwise maintain an address and/or other identification information for the remote device 814 on the second network 812. In this regard, the second network 812 may be physically and/or logically distinct from the network 810, such as, for example, the Internet, a cellular network, a wide area network (WAN), or the like. The remote device 814 generally represents a server or other computing device configured to receive and analyze or otherwise monitor measurement data, event log data, and potentially other information obtained for the patient associated with the medical device 802. In exemplary embodiments, the remote device 814 is coupled to a database 816 configured to store or otherwise maintain data associated with individual patients. In practice, the remote device 814 may reside at a location that is physically distinct and/or separate from the medical device 802 and the client device 806, such as, for example, at a facility that is owned and/or operated by or otherwise affiliated with a manufacturer of the medical device 802. For purposes of explanation, but without limitation, the remote device 814 may alternatively be referred to herein as a server.

Still referring to FIG. 8, the sensing element 804 generally represents the component of the patient monitoring system 800 that is configured to generate, produce, or otherwise output one or more electrical signals indicative of a physiological condition that is sensed, measured, or otherwise quantified by the sensing element 804. In this regard, the physiological condition of a user influences a characteristic of the electrical signal output by the sensing element 804, such that the characteristic of the output signal corresponds to or is otherwise correlative to the physiological condition that the sensing element 804 is sensitive to. In exemplary embodiments, the sensing element 804 is realized as an interstitial glucose sensing element inserted at a location on the body of the patient that generates an output electrical signal having a current (or voltage) associated therewith that is correlative to the interstitial fluid glucose level that is sensed or otherwise measured in the body of the patient by the sensing element 804.

The medical device 802 generally represents the component of the patient monitoring system 800 that is communicatively coupled to the output of the sensing element 804 to receive or otherwise obtain the measurement data samples from the sensing element 804 (e.g., the measured glucose and characteristic impedance values), store or otherwise maintain the measurement data samples, and upload or otherwise transmit the measurement data to the server 814 via the client device 806. In one or more embodiments, the medical device 802 is realized as an infusion device 102, 200, 502 configured to deliver a fluid, such as insulin, to the body of the patient. That said, in other embodiments, the medical device 802 could be a standalone sensing or monitoring device separate and independent from an infusion device (e.g., sensing arrangement 104, 504), such as, for example, a continuous glucose monitor (CGM) or similar device. It should be noted that although FIG. 8 depicts the medical device 802 and the sensing element 804 as separate components, in practice, the medical device 802 and the sensing element 804 may be integrated or otherwise combined to provide a unitary device that can be worn by the patient.

In exemplary embodiments, the medical device 802 includes a control module 822, a data storage element 824 (or memory), and a communications interface 826. The control module 822 generally represents the hardware, circuitry, logic, firmware and/or other component(s) of the medical device 802 that is coupled to the sensing element 804 to receive the electrical signals output by the sensing element 804 and perform or otherwise support various additional tasks, operations, functions and/or processes described herein. Depending on the embodiment, the control module 822 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In some embodiments, the control module 822 includes an analog-to-digital converter (ADC) or another similar sampling arrangement that samples or otherwise converts an output electrical signal received from the sensing element 804 into corresponding digital measurement data value. In other embodiments, the sensing element 804 may incorporate an ADC and output a digital measurement value.

The communications interface 826 generally represents the hardware, circuitry, logic, firmware and/or other components of the medical device 802 that are coupled to the control module 822 for outputting data and/or information from/to the medical device 802 to/from the client device 806. For example, the communications interface 826 may include or otherwise be coupled to one or more transceiver modules capable of supporting wireless communications between the medical device 802 and the client device 806. In exemplary embodiments, the communications interface 826 is realized as a Bluetooth transceiver or adapter configured to support Bluetooth Low Energy (BLE) communications.

In exemplary embodiments, the remote device 814 receives, from the client device 806, measurement data values associated with a particular patient (e.g., sensor glucose measurements, acceleration measurements, and the like) that were obtained using the sensing element 804, and the remote device 814 stores or otherwise maintains the historical measurement data in the database 816 in association with the patient (e.g., using one or more unique patient identifiers). Additionally, the remote device 814 may also receive, from or via the client device 806, meal data or other event log data that may be input or otherwise provided by the patient (e.g., via client application 808) and store or otherwise maintain historical meal data and other historical event or activity data associated with the patient in the database 816. In this regard, the meal data include, for example, a time or timestamp associated with a particular meal event, a meal type or other information indicative of the content or nutritional characteristics of the meal, and an indication of the size associated with the meal. In exemplary embodiments, the remote device 814 also receives historical fluid delivery data corresponding to basal or bolus dosages of fluid delivered to the patient by an infusion device 102, 200, 502. For example, the client application 808 may communicate with an infusion device 102, 200, 502 to obtain insulin delivery dosage amounts and corresponding timestamps from the infusion device 102, 200, 502, and then upload the insulin delivery data to the remote device 814 for storage in association with the particular patient. The remote device 814 may also receive geolocation data and potentially other contextual data associated with a device 802, 806 from the client device 806 and/or client application 808, and store or otherwise maintain the historical operational context data in association with the particular patient. In this regard, one or more of the devices 802, 806 may include a global positioning system (GPS) receiver or similar modules, components or circuitry capable of outputting or otherwise providing data characterizing the geographic location of the respective device 802, 806 in real-time. Similarly, in some embodiments, one or more of the devices 802, 806 may include an environmental sensing arrangement or similar modules, components or circuitry capable of outputting or otherwise providing data characterizing the current operating environment in real-time.

The historical patient data may be analyzed by one or more of the remote device 814, the client device 806, and/or the medical device 802 to alter or adjust operation of an infusion device 102, 200, 502 to influence fluid delivery in a personalize manner. For example, the patient's historical meal data and corresponding measurement data or other contextual data may be analyzed to predict a future time when the next meal is likely to be consumed by the patient, the likelihood of a future meal event within a specific time period, the likely size or amount of carbohydrates associated with a future meal, the likely type or nutritional content of the future meal, and/or the like. Moreover, the patient's historical measurement data for postprandial periods following historical meal events may be analyzed to model or otherwise characterize the patient's glycemic response to the predicted size and type of meal for the current context (e.g., time of day, day of week, geolocation, etc.). One or more aspects of the infusion device 102, 200, 502 that control or regulate insulin delivery may then be modified or adjusted to proactively account for the patient's likely meal activity and glycemic response.

In one or more exemplary embodiments, the remote device 814 utilizes machine learning to determine which combination of historical sensor glucose measurement data, historical delivery data, historical auxiliary measurement data (e.g., historical acceleration measurement data, historical heart rate measurement data, and/or the like), historical event log data, historical geolocation data, and other historical or contextual data are correlated to or predictive of the occurrence of a particular event, activity, or metric for a particular patient, and then determines a corresponding equation, function, or model for calculating the value of the parameter of interest based on that set of input variables. Thus, the model is capable of characterizing or mapping a particular combination of one or more of the current (or recent) sensor glucose measurement data, auxiliary measurement data, delivery data, geographic location, patient behavior or activities, and the like to a value representative of the current probability or likelihood of a particular event or activity or a current value for a parameter of interest. It should be noted that since each patient's physiological response may vary from the rest of the population, the subset of input variables that are predictive of or correlative for a particular patient may vary from other users. Additionally, the relative weightings applied to the respective variables of that predictive subset may also vary from other patients who may have common predictive subsets, based on differing correlations between a particular input variable and the historical data for that particular patient. It should be noted that any number of different machine learning techniques may be utilized by the remote device 814 to determine what input variables are predictive for a current patient of interest, such as, for example, artificial neural networks, genetic programming, support vector machines, Bayesian networks, probabilistic machine learning models, or other Bayesian techniques, fuzzy logic, heuristically derived combinations, or the like.

In one or more embodiments described herein, a patient (or other user) utilizes the client application 808 at the client device 806 to plan his or her daily activities (e.g., meals, insulin boluses, exercise) and/or obtain recommendations pertaining to the management or control of the patient's glucose levels. In such embodiments, the client device 806 may receive recent, contemporaneous, or real-time data characterizing the current state of the patient from the infusion device 802 and/or sensing element 804 and utilize the received data characterizing the current patient state to generate predictions of the patient's future glucose levels and/or generate recommendations for activities that the patient could engage in to improve his or her condition. In this regard, the client device 806 may also receive or otherwise obtain, from the remote device 814 and/or database 816 via the network 812, historical data or models based thereon for calculating future glucose levels or otherwise generating recommendations in a manner that is influenced by historical data. Planning GUI displays or other graphical indicia of recommended activities (and recommended attributes therefor) may be generated, displayed, or otherwise presented by the client application 808 at the client device 806.

In various embodiments, the patient may utilize the GUI displays (or GUI elements thereof) of the client application 808 at the client device 806 to review recommendations, accept or confirm recommendations, modify recommendations, and/or otherwise plan his or her daily activities. Thereafter, the client application 808 at the client device 806 may communicate with one or more of the infusion device 802 and/or the remote device 814 to implement or otherwise effectuate the recommendations or other planned activities. For example, the client application 808 at the client device 806 may instruct or otherwise configure the infusion device 802 to deliver a recommended bolus of insulin or schedule a future delivery of insulin based on the patient's activity plan. The client application 808 at the client device 806 may also upload the patient's activity plan to the remote device 814, which, in turn may support various notification processes (e.g., by pushing reminders or instructions to various devices 802, 806 at appropriate times) or otherwise support the subject matter described herein (e.g., by implementing processing or automation tasks at the remote device 814 rather than the client device 806 or elsewhere within the system 800). For example, in some embodiments, data indicative of the current patient state may be uploaded or otherwise transmitted to the remote device 814 from the client device 806, with the remote device 814 performing various processing tasks with respect to the received data and providing resulting recommendations, predictions, and or the like back to the client device 806 for presentation by the client application 808.

Patient Day Planning

Figure 9:
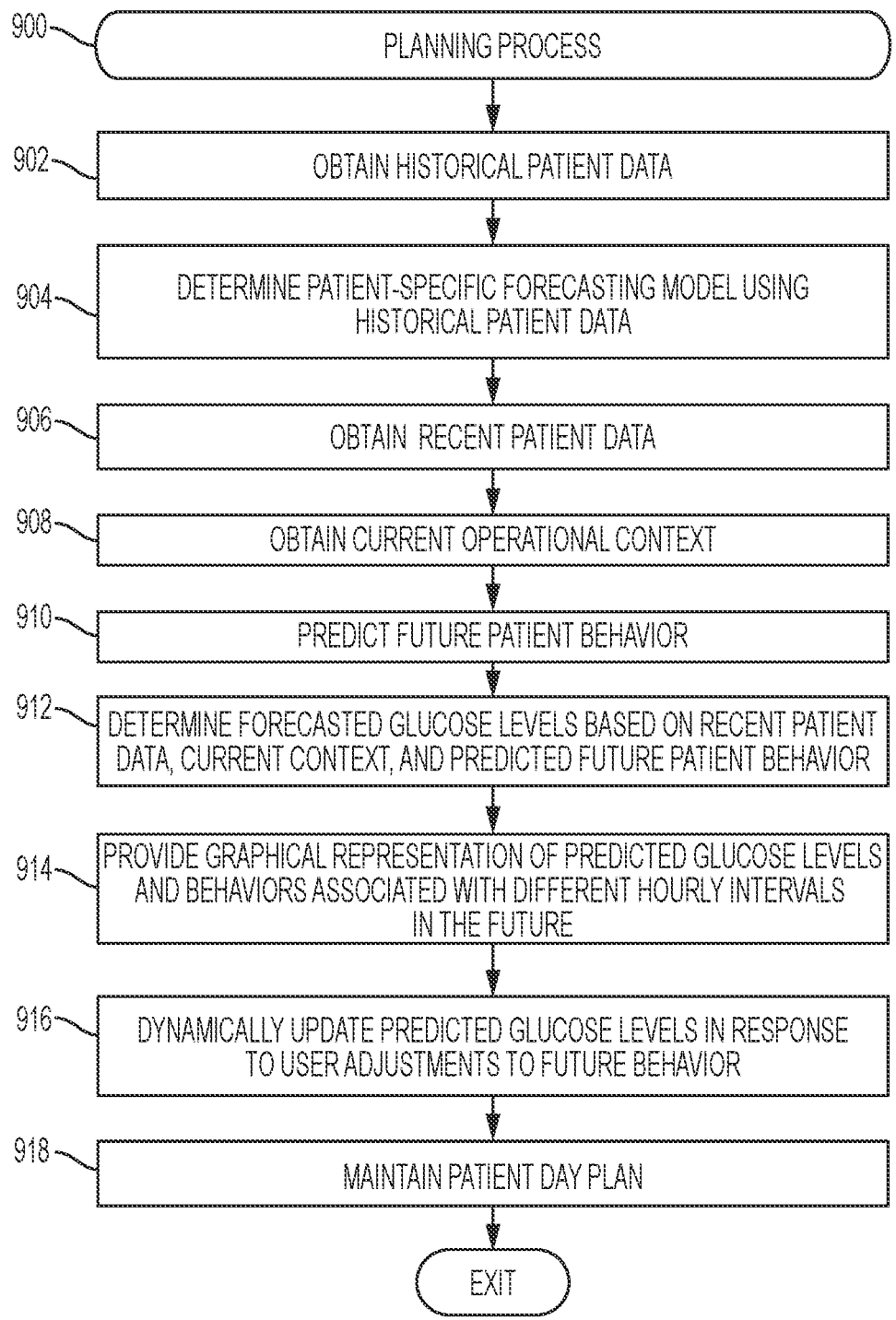
FIG. 9 is a flow diagram of an exemplary planning process suitable implementation in connection with a patient monitoring system in one or more exemplary embodiments.

FIG. 9 depicts an exemplary planning process 900 suitable for implementation in an infusion system or other patient monitoring system to prospectively manage the physiological condition of a patient by planning his or her daily activities in advance. The various tasks performed in connection with the planning process 900 may be performed by hardware, firmware, software executed by processing circuitry, or any combination thereof. For illustrative purposes, the following description refers to elements mentioned above in connection with FIGS. 1-8. In practice, portions of the planning process 900 may be performed by different elements of an infusion system, such as, for example, an infusion device 102, 200, 502, 802, a client computing device 106, 806, a remote computing device 108, 814, and/or a pump control system 520, 600. It should be appreciated that the planning process 900 may include any number of additional or alternative tasks, the tasks need not be performed in the illustrated order and/or the tasks may be performed concurrently, and/or the planning process 900 may be incorporated into a more comprehensive procedure or process having additional functionality not described in detail herein. Moreover, one or more of the tasks shown and described in the context of FIG. 9 could be omitted from a practical embodiment of the planning process 900 as long as the intended overall functionality remains intact.

In exemplary embodiments, the planning process 900 utilizes a patient-specific forecasting model to forecast a patient's physiological condition for discrete time periods or intervals into the future based on the current state of the patient's physiological condition and predicted activity or behavior by the patient in the future. In the illustrated embodiment, the planning process 900 retrieves or otherwise obtains historical data associated with the patient of interest to be modeled and develops, trains, or otherwise determines a forecasting model for the patient using the historical data associated with the patient (tasks 902, 904). For example, as described in U.S. patent application Ser. No. 15/933,264, historical patient data associated with the patient may be retrieved or otherwise obtained from the database 816 and the relationship between different subsets of the historical patient data may be analyzed to create a patient-specific forecasting model associated with that patient. Depending on the embodiment, the patient-specific forecasting model may be stored on the database 816 in association with the patient and utilized by the server 814 to determine a glucose forecast for the patient (e.g., in response to a request from a client device 806) and provide the resulting glucose forecast to a client device 806 for presentation to a user. In other embodiments, the server 814 pushes, provides, or otherwise transmits the patient-specific forecasting model to one or more electronic devices 802, 806 associated with the patient (e.g., infusion device 502) for implementing and supporting glucose forecasts at the end user device (e.g., by prediction engine 608).

In one or more exemplary embodiments, a recurrent neural network is utilized to create hourly neural network cells that are trained to predict an average glucose level for the patient associated with that respective hourly interval based on subsets of historical patient data corresponding to that hourly interval across a plurality of different days preceding development of the model. For example, in one embodiment, for each hourly interval within a day, a corresponding long short-term memory (LSTM) unit (or cell) is created, with the LSTM unit outputting an average glucose value for that hourly interval as a function of the subset of historical patient data corresponding to that hourly interval and the variables from one or more of the LSTM units preceding the current LSTM unit. In this regard, the model for a particular hourly interval is capable of characterizing or mapping the insulin delivery data during the hourly interval, the meal data during the hourly interval, the exercise data during the hourly interval, and the average glucose value for the preceding hourly interval to the average sensor glucose value for the hourly interval being modeled. It should be noted that any number of different machine learning techniques may be utilized to determine what input variables are predictive for a current patient of interest and a current hourly interval of the day, such as, for example, artificial neural networks, genetic programming, support vector machines, Bayesian networks, probabilistic machine learning models, or other Bayesian techniques, fuzzy logic, heuristically derived combinations, or the like. Additionally, it should be noted that the subject matter described herein is not necessarily limited to hourly forecasting or modeling, and could be implemented in an equivalent manner for smaller or larger periods or increments of time.

The planning process 900 continues by receiving, retrieving, or otherwise obtaining recent patient data, identifying or otherwise obtaining the current operational context associated with the patient, and predicting future behavior of the patient based on the recent patient data and the current operational context (tasks 906, 908, 910). In this regard, predictive models for future insulin deliveries, future meals, future exercise events, and/or future medication dosages may be determined that characterize or map a particular combination of one or more of the current (or recent) sensor glucose measurement data, auxiliary measurement data, delivery data, geographic location, meal data, exercise data, patient behavior or activities, and the like to a value representative of the current probability or likelihood of a particular event or activity and/or a current value associated with that event or activity (e.g., a predicted meal size, a predicted exercise duration and/or intensity, a predicted bolus amount, and/or the like). Thus, the planning process 900 may obtain from one or more of the sensing arrangements 504, 506, 508 the infusion device 502 and/or the database 816 the current or most recent sensor glucose measurement values associated with the patient, along with data or information quantifying or characterizing recent insulin deliveries, meals, exercise, and potentially other events, activities or behaviors by the user within a preceding interval of time (e.g., within the preceding 2 hours). The planning process 900 may also obtain from one or more of the sensing arrangements 550, 560, the infusion device 502 and/or the database 816 data or information quantifying or characterizing the current or recent operational contexts associated with the infusion device 502.

Based on the current and recent patient measurement data, insulin delivery data, meal data, and exercise data, along with the current time of day, the current day of the week, and/or other current or recent context data, the planning process 900 determines event probabilities and/or characteristics for future hourly time intervals. For example, for each hourly time interval in the future, the planning process 900 may determine a meal probability and/or a predicted meal size during that future hourly time interval that may be utilized as an input to the LSTM unit for that hourly time interval. Similarly, the planning process 900 may determine a predicted insulin delivery amount, a predicted exercise probability and/or a predicted exercise intensity or duration, a predicted medication dosage, and/or the like during each respective future hourly time interval based on the relationships between the recent patient data and context data and historical patient data and context data preceding occurrence of previous instances of those events. Some examples of predicting patient behaviors or activities are described in U.S. patent application Ser. No. 15/847,750.

After predicting future patient behavior likely to influence the patient's future glucose levels, the planning process 900 continues by calculating or otherwise determining forecasted glucose levels for hourly intervals in the future based at least in part on the current or recent glucose measurement data and the predicted future behavior and generating or otherwise providing graphical representations of the forecasted glucose levels associated with the different future hourly intervals (tasks 912, 914). Based on the current time of day, the forecasting model for the next hourly interval of the day may be selected and utilized to calculate a forecasted glucose level for that hourly interval based at least in part on the recent sensor glucose measurement value(s) and the predicted meals, exercise, insulin deliveries and/or medication dosages for the next hourly interval of the day. For example, the current sensor glucose measurement value and preceding sensor glucose measurement values obtained within the current hourly interval may be averaged or otherwise combined to obtain an average sensor glucose measurement value for the current hourly interval that may be input to the forecasting model for the next hourly interval of the day. The forecasting model is then utilized to calculate a forecasted average glucose value for the next hourly interval of the day based on that average sensor glucose measurement value for the current hourly interval and the predicted patient behavior during the next hourly interval. The forecasted average glucose value for the next hourly interval may then be input to the forecasting model for the subsequent hourly interval for calculating a forecasted glucose value for that subsequent hourly interval based on its associated predicted patient behavior, and so on.

Figure 10:
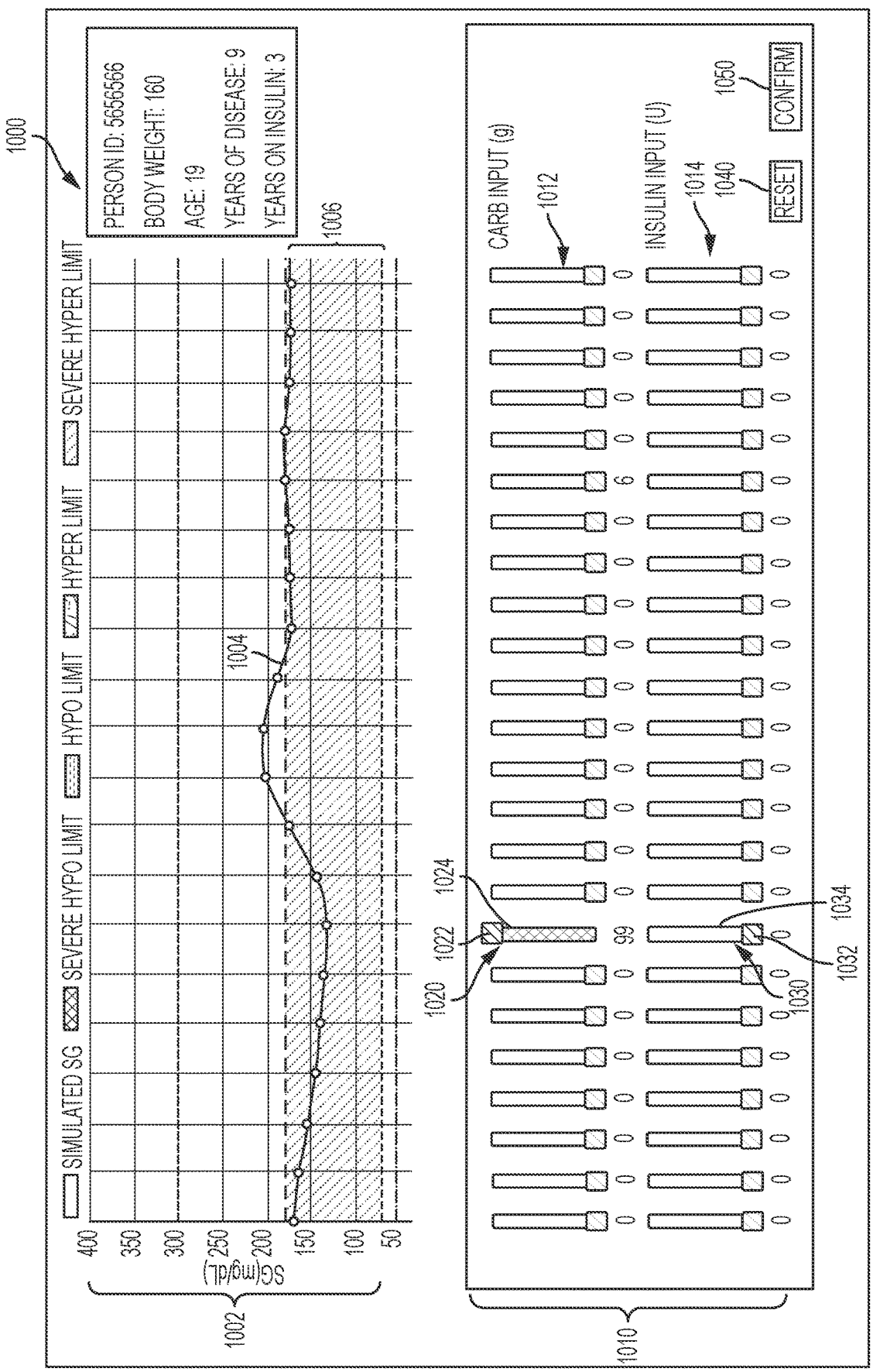
FIGS. 10-11 depict exemplary planning graphical user interface (GUI) displays suitable for presentation on a display device in connection with one or more exemplary embodiments of the planning process of FIG. 9.

FIG. 10 depicts an exemplary planning GUI display 1000 including a glucose forecast region 1002 that includes graphical representations of forecasted glucose levels for a patient in association with subsequent hourly intervals of the day. In the illustrated GUI display 1000, the glucose forecast region 1002 includes a line chart or line graph 1004 of the patient's forecasted hourly glucose values with a visually distinguishable overlay region 1006 that indicates a target range for the patient's glucose level. Depending on the embodiment, the planning GUI display 1000 may be presented on a display device 540 associated with a medical device 102, 502, 802 or on another electronic device 806 within a patient monitoring system 800. In one or more embodiments, the planning GUI display 1000 is generated or otherwise provided in response to a patient selecting a GUI element configured to initiate a day planning application or process at a client device 806.

The planning GUI display 1000 also includes an activity forecast region 1010 that includes graphical representations of activities or events that the patient is likely to experience within the planning time period at the respective timings within the planning time period when those activities or events are likely to occur. In exemplary embodiments, the activity forecast region 1010 includes, for each hourly interval having an associated forecast glucose value, a plurality of adjustable GUI elements associated with that respective hourly interval, where each of the adjustable GUI elements is associated with a different type of activity or event. For example, the illustrated embodiment includes a first set of adjustable GUI elements 1012 corresponding to a meal event associated with a respective hourly time interval and a second set of adjustable GUI elements 1014 corresponding to an insulin bolus event associated with a respective hourly time interval. The state, position, or other aspect of the GUI elements 1012, 1014 is adjustable and configured to indicate an amount, characteristic, or other attribute associated with a respective event at a respective hourly time interval. For example, in the illustrate embodiment, the GUI elements 1012, 1014 are realized as vertically-oriented sliders, where the relative position of the slider with respect to the slider bar indicates the amount associated with a respective meal event or bolus event. For example, in the illustrated embodiment, the adjustable sliding indicator 1022 for the meal event slider 1020 associated with an hourly time interval occurring seven hours into the future is positioned with respect to its slider bar 1024 to indicate an amount of carbohydrates associated with a meal event that is likely to occur at or within an hourly time interval 7 hours into the future. In one or more embodiments, upon initial presentation of the planning GUI display 1000, each of the displayed GUI elements 1012, 1014 is initially positioned or otherwise configured to indicate the predicted attribute or characteristic for an activity or event that is predicted for the patient for a particular hourly interval based on the patient's historical data.

Referring again to FIG. 9, in exemplary embodiments, the planning process 900 dynamically updates the graphical representations of the forecasted glucose levels associated with the different future hourly intervals in response to user adjustments to the patient's future behavior (task 916). In this regard, the GUI elements provided on the planning GUI display allow the patient or other user to adjust attributes or characteristics associated with activities or events the patient is likely to engage in, or to add or remove activities or events within the planning time period. In response to an adjustment to the patient's future behavior, the forecasted glucose levels for the patient are dynamically updated to reflect the change to the inputs to the patient's forecasting model.

Figure 11:
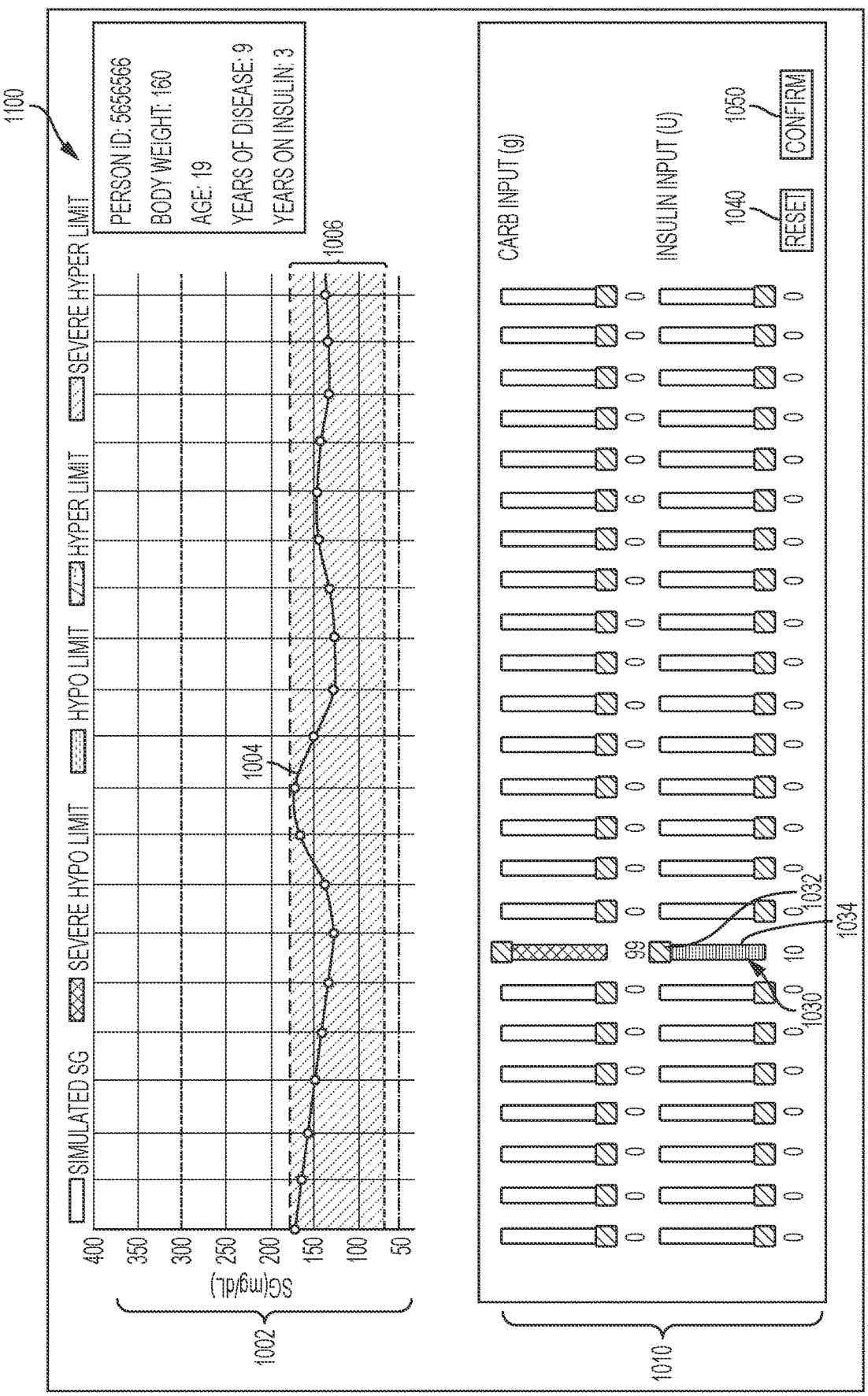

For example, referring now to FIGS. 10-11, in response to an adjustment to the bolus event slider 1030 associated with an hourly time interval occurring seven hours into the future, a corresponding bolus amount of insulin may be input to the patient's forecasting model at the hourly time interval occurring seven hours into the future (e.g., by inputting the bolus amount of insulin to the LSTM cell corresponding to seven hours into the future), thereby influencing the patient's forecasted glucose levels thereafter. The patient (or other user) reviewing the initial planning GUI display 1000 may confirm that the initially predicted meal event timing and amount indicated by the slider indicator 1022 is likely or desirable, and as a result, may leave the slider indicator 1022 in its initial position with respect to its slider bar 1024. Alternatively, if the patient believes the predicted meal is unlikely or undesirable, the patient may select a button or similar selectable GUI element 1040 to remove the predicted meal event from the patient's activity plan.

In the illustrated embodiment, when the patient determines that the initially predicted meal event is likely or desirable, the patient may also identify that the predicted meal results in a postprandial spike in the patient's glucose levels that exceeds the upper limit of the patient's target range indicated by the overlay region 1006 (e.g., 170 mg/dL). To mitigate the forecasted postprandial hyperglycemia, the patient may adjust the bolus amount slider indicator 1032 for the hourly time interval occurring seven hours into the future to gradually increase a meal bolus amount to be administered at or around the predicted meal event. As the patient adjusts the bolus amount slider indicator 1032 upward with respect to its slider bar 1034 to increase the bolus amount, the planning process 900 dynamically updates the forecasted glucose values for the contemporaneous and subsequent hourly intervals to reflect the bolus amount and then dynamically updates forecasted glucose level graph 1004 to reflect the updated forecasted glucose values. As the forecasted glucose level graph 1004 is updated to reduce the postprandial forecasted glucose values, the patient may continue adjusting bolus amount slider indicator 1032 to progressively increase the bolus amount until the postprandial forecasted glucose values are within the target overlay region 1006. In exemplary embodiments, the portion of the slider bar 1034 below the slider indicator 1032 is rendered using visually distinguishable characteristic (e.g., color, fill pattern, or the like) relative to the remaining portion of the slider bar 1034 above the slider indicator 1032.

Referring again to FIG. 9, in exemplary embodiments, the planning process 900 stores or otherwise maintains the resulting plan for the patient's future activity or behavior for reference during subsequent monitoring of the patient's physiological condition (task 918). For example, in response to the patient or other user selecting a button or similar selectable GUI element 1050 to validate or otherwise confirm the depicted activity plan and corresponding glucose forecast, the planning process 900 may store or otherwise maintain (e.g., in memory 606, the database 816, and/or local storage associated with another device 102, 104, 106, 108, 802, 806, 814) the patient's activity plan that maintains an association between a planned activity, the planned timing associated with the planned activity, and the planned attributes or characteristics associated with that planned activity for each of the activities indicated via the planning GUI display along with the forecasted glucose values for the patient and their respective timings. It should be noted that the patient activity plan and related processes described herein are not limited to meals, boluses, medications, exercise, sleep, or other events, and depending on the embodiment, may be implemented in an equivalent manner with respect to any number of different patient experiences or actions, or in connection with attributes or metrics associated with a respective activity (e.g., meal content, meal size, meal time of day, etc.). Additionally, although not illustrated in FIG. 9, in practice, the forecasting model may be periodically validated to verify accuracy and identify when the forecasting model may need to be retrained, in which case an updated patient-specific forecasting model may be determined based on historical patient data that postdates development of the current patient-specific forecasting model.

As described in greater detail below in the context of FIG. 12, the patient's activity plan may serve as a reference for the patient's subsequent behavior and glucose levels that may be utilized to generate reminders, recommendations, and/or the like to encourage the patient to adhere to the activity plan or otherwise minimize the deviations between the patient's actual behavior and/or glucose levels and the preplanned behavior and/or glucose levels. In this regard, the patient, the patient's care provider, or other user may utilize the planning GUI display to plan out the patient's meals, insulin boluses, exercise, sleep, and/or other daily activities to achieve a forecasted glucose outcome aligned with a desired glucose outcome for the patient (e.g., maintaining glucose levels within a target range, minimizing risk of hypoglycemia and/or hyperglycemia, and/or the like). It should be noted that although FIGS. 10-11 depict an embodiment of a planning GUI display including only GUI elements for adjusting meal event carbohydrate amounts and insulin bolus amounts for purposes of explanation, in practice, additional GUI elements may be present to plan exercise events (e.g., by defining timing, duration and/or intensity), sleep events (e.g., timing and duration thereof), and potentially other activities that are likely to influence the patient's glucose level. The patient's day plan may then be utilized to steer or otherwise navigate the patient's future behavior to best achieve the desired glucose outcome as planned, for example, by generating reminders to consume a meal, engage in exercise, administer an insulin bolus, or the like and/or generating recommendations to minimize the deviations between the patient's actual glucose levels and the planned glucose levels.

The planning process 900 and related planning GUI displays described herein solve the technical problem of enabling a patient to efficiently visualize and quickly understand how his or her glucose levels are likely to respond to the patient's daily activities and fluctuate throughout the day on an individual GUI display that does not require users drill down through many layers or navigate through multiple different views. A patient may create a daily activity plan that achieves the desired tradeoff between control or management of the patient's glucose level and the amount of activity or effort required by the patient to manage his or her condition. Additionally, the patient can better understand and account for unusual or atypical activities or behaviors (e.g., an abnormally large meal or a meal at an unusual amount of time, an unusually prolonged period of exercise, or the like) may affect his or her glucose levels in advance and plan accordingly. By converting what would otherwise be guesswork-heavy daily glucose management processes into a concise GUI display that leverages historical patient data and provides dynamic real-time feedback, the cognitive burden on patients when planning one's day may be reduced while also improving patient outcomes. Such GUI displays may also be utilized to assist the patient's doctor(s) or other healthcare provider(s) in describing the impact of the patient's behaviors and medications on the patient's glycemic control. The planning GUI displays may also be utilized to depict deviations between the patient's current glucose level and other activities or contextual data characterizing the patient's current situation with respect to a preplanned activity plan to assist in developing a corrective plan to restore the patient's glycemic condition to the previous trajectory (e.g., how quickly or how long it will take to return to the planned trajectory, how to avoid overcorrection, etc.).

Figure 12:
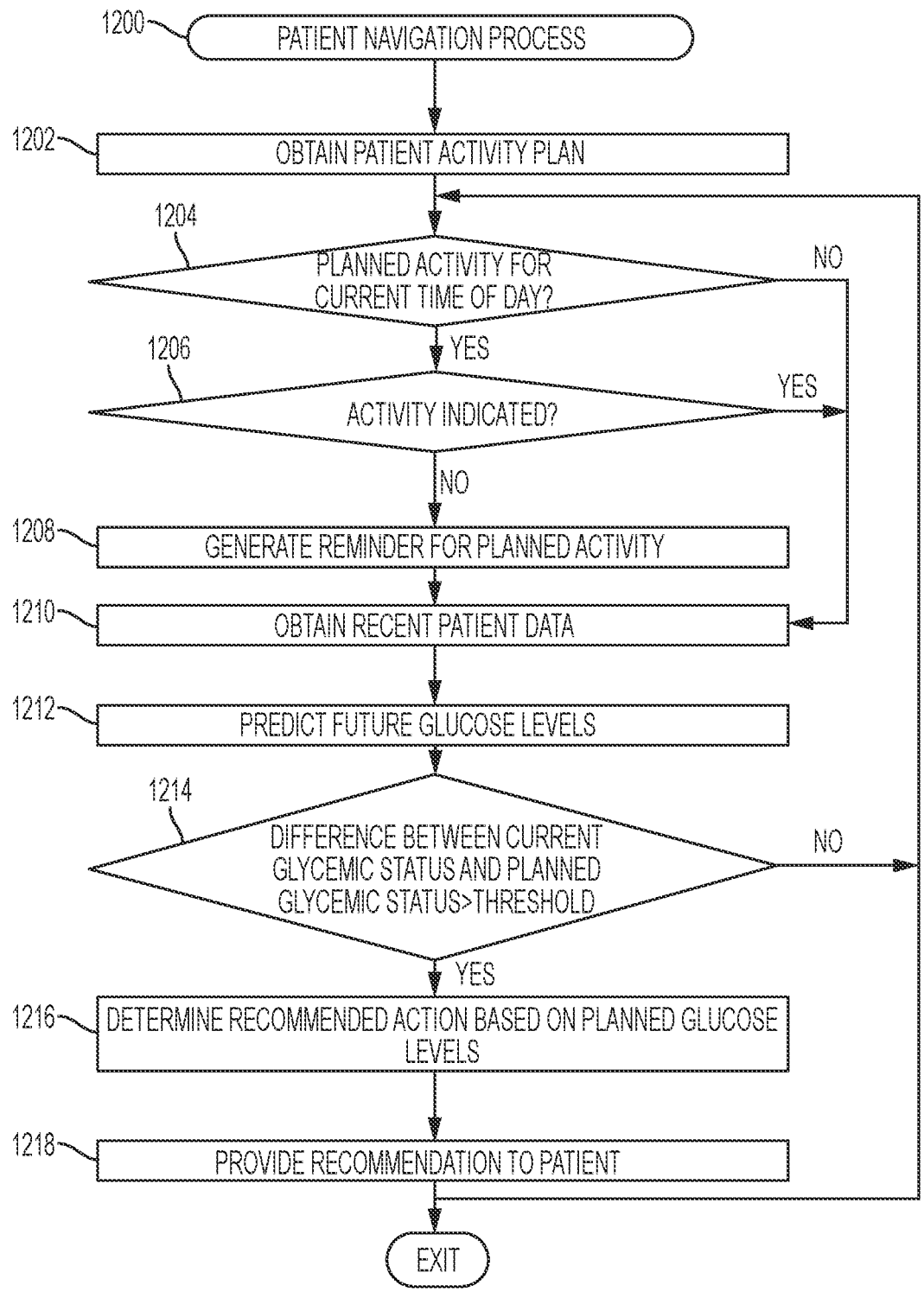
FIG. 12 is a flow diagram of an exemplary patient navigation process suitable implementation in connection with the planning process of FIG. 9 in one or more exemplary embodiments.

FIG. 12 depicts an exemplary patient navigation process 1200 suitable for implementation in an infusion system or other patient monitoring system to provide guidance for managing the physiological condition of a patient in accordance with a predetermined activity plan for the patient. The various tasks performed in connection with the patient navigation process 1200 may be performed by hardware, firmware, software executed by processing circuitry, or any combination thereof. For illustrative purposes, the following description refers to elements mentioned above in connection with FIGS. 1-8. In practice, portions of the patient navigation process 1200 may be performed by different elements of an infusion system, such as, for example, an infusion device 102, 200, 502, 802, a client computing device 106, 806, a remote computing device 108, 814, and/or a pump control system 520, 600. It should be appreciated that the patient navigation process 1200 may include any number of additional or alternative tasks, the tasks need not be performed in the illustrated order and/or the tasks may be performed concurrently, and/or the patient navigation process 1200 may be incorporated into a more comprehensive procedure or process having additional functionality not described in detail herein. Moreover, one or more of the tasks shown and described in the context of FIG. 12 could be omitted from a practical embodiment of the patient navigation process 1200 as long as the intended overall functionality remains intact.

The patient navigation process 1200 initializes or begins by retrieving or otherwise obtaining an activity plan for a patient to be used as a reference for providing guidance to the patient (task 1202). In this regard, the stored activity plan configured for a patient using the planning GUI display may be obtained by a client application 808 at a client device 806 associated with the patient, either from local memory of the client device 806 or from the database 816 via the remote device 814 and network 812. As described above, the activity plan maintains an association between preplanned activities for the patient, the planned timing associated with the respective activities, and the planned attributes or characteristics associated with respective activities along with the forecasted glucose values for the patient and their respective timings.

In exemplary embodiments, the patient navigation process 1200 continually monitors the current time of day, the current physiological condition of the patient, and/or other activities engaged in by the patient in comparison to the patient's activity plan and generates or otherwise provides user notifications in response to deviations from the patient's activity plan. In this regard, the patient navigation process 1200 utilizes the current time of day to determine whether a preplanned activity for the patient is associated with the time interval encompassing the current time of day (task 1204). In the illustrated embodiment, when the current time of day corresponds to a time interval having a preplanned activity associated therewith, the patient navigation process 1200 determines whether the activity has been indicated before generating or otherwise providing a reminder that indicates the preplanned activity to the patient (tasks 1206, 1208). For example, referring again to FIGS. 10-11, the patient may utilize the planning GUI display 1000, 1100 to create a daily plan for his or her activities at upon waking up at 6 AM. At 1 PM (e.g., 7 hours later), a client application 808 at a client device 806 implementing the patient navigation process 1200 may identify that there is a preplanned meal event and a preplanned insulin bolus associated with the current time of day, and check to see whether the patient has announced a meal corresponding to the preplanned meal event or administered an insulin bolus corresponding to the preplanned insulin bolus. In this regard, the client application 808 may check for announced events within a threshold period of time in advance of the current time (e.g., within the last 30 minutes). In some embodiments, the client application 808 may analyze measurement data from one or more sensing arrangements 504, 506, 508, 550, 560 to determine whether a preplanned activity has occurred (e.g., identifying exercise based on acceleration measurement data, heart rate data, and/or the like).

In the absence of indication of the preplanned activity having occurred, the client application 808 may generate or otherwise provide a graphical notification on the client device 806 that identifies, for the patient, the type of activity that was planned for the patient at the current time of day along with the planned attributes associated with that activity. For example, if the patient has announced a meal within the threshold period of time but there is no indication that the patient has administered the planned insulin bolus, the client application 808 may generate or otherwise provide a graphical notification on the client device 806 that reminds the patient to administer a bolus of 10 units of insulin to maintain adherence with the patient's day plan. Similarly, if the patient's day plan called for the patient to engage in exercise at or around the current time of day, and the patient's heart rate measurement data and acceleration measurement data do not indicate an exercise event, the client application 808 may generate or otherwise provide a graphical notification on the client device 806 that reminds the patient to engage in exercise for the preplanned duration. In this regard, in some embodiments where the patient's measurement data indicates the patient has or is currently engaged in exercise but for a duration that is less than the preplanned duration, the client application 808 may generate or otherwise provide a graphical notification on the client device 806 that reminds the patient of the planned duration for the exercise the patient is currently engaged in.

As noted above, in exemplary embodiments, the patient navigation process 1200 also continually monitors the physiological condition of the patient and generates or otherwise provides user notifications in response to deviations from the patient's planned physiological condition at the current time of day. In this regard, the patient navigation process 1200 receives or otherwise obtains recent patient data, calculates or otherwise determines predicted future glucose levels, and verifies the current and predicted future glucose levels are within a threshold difference from the preplanned glucose levels at the corresponding times of day (tasks 1210, 1212, 1214). Based on the patient's current glucose measurement value, current insulin on board, and other current or recent patient measurement data, insulin delivery data, meal data, and exercise data, and the like, the client application 808 may calculate or otherwise determine one or more predicted future glucose values for the patient at one or more times (or time periods) in the future. For example, the client application 808 may determine forecast glucose values for the patient for the next four hourly intervals.

In the illustrated embodiment, when the difference between the current glucose measurement value and the originally forecasted glucose value for the current hourly time interval is greater than a threshold and/or when the difference between the one or more forecasted glucose values for subsequent hourly intervals determined based on the current patient state and the originally forecasted glucose value(s) for the respective hourly time interval(s) is greater than a threshold, the patient navigation process 1200 identifies or otherwise determines one or more recommended remedial actions for the patient to compensate for the deviation from the patient's activity plan based on the planned glucose levels and notifies the patient of the recommended action (tasks 1216, 1218). For example, when the current and/or predicted future glucose levels for the patient are less than the originally planned glucose levels by more than a threshold amount, the client application 808 may generate or otherwise provide a graphical notification on the client device 806 that indicates the patient should consume carbohydrates to adjust or otherwise redirect the patient's glycemic state back towards the patient's activity plan. Conversely, if the current and/or predicted future glucose levels for the patient are greater than the originally planned glucose levels by more than a threshold amount, the client application 808 may generate or otherwise provide a graphical notification on the client device 806 that indicates the patient should administer an insulin bolus. It should be noted that there are numerous different techniques for quantifying and weighting the differences between sets of numerical values, and the subject matter described herein is not intended to be limited to any particular scheme or manner for determining a metric indicative of a deviation between a patient's current glycemic status and the originally planned glycemic status. Additionally, in some embodiments, in addition to monitoring the relationship between the current glucose levels and originally forecast glucose levels, the patient navigation process 1200 may also generate or otherwise provide recommendations when the current and/or predicted future glucose levels for the patient are outside of the target range for the patient.

For example, referring again to FIGS. 10-11, if at 4 PM, the postprandial response in the patient's glucose level results in the patient's current glucose measurement value exceeding the forecasted glucose level for 4 PM by more than a threshold or otherwise exceeding the upper limit of the target range 1006 (e.g., 170 mg/dL), the client application 808 may generate a recommendation that the patient administer a correction bolus to reduce his or her glucose levels back towards the originally planned levels at the current and/or subsequent times of day. In one or more embodiments, a button or similar selectable GUI element may be presented in conjunction with the recommendation that is selectable by the patient to confirm or otherwise accept the recommendation. In response to confirmation of a recommended insulin bolus amount, the client application 808 at the client device 806 may transmit or otherwise provide instructions to the infusion device 802 via network 810 that indicates the recommended insulin bolus amount to be delivered. In response, the pump control system 520, 600 may respond by generating corresponding commands for operating the motor 532 to deliver the recommended amount of insulin. In exemplary embodiments, the patient navigation process 1200 repeats continually throughout operation of a medical device 102, 502, 802 to provide reminders or recommendations to the patient as needed to improve adherence to the patient's daily activity plan or otherwise minimize deviations from the patient's originally planned glucose levels throughout the day.

Data-Driven Outcome-Optimized Recommendations

Figure 13:
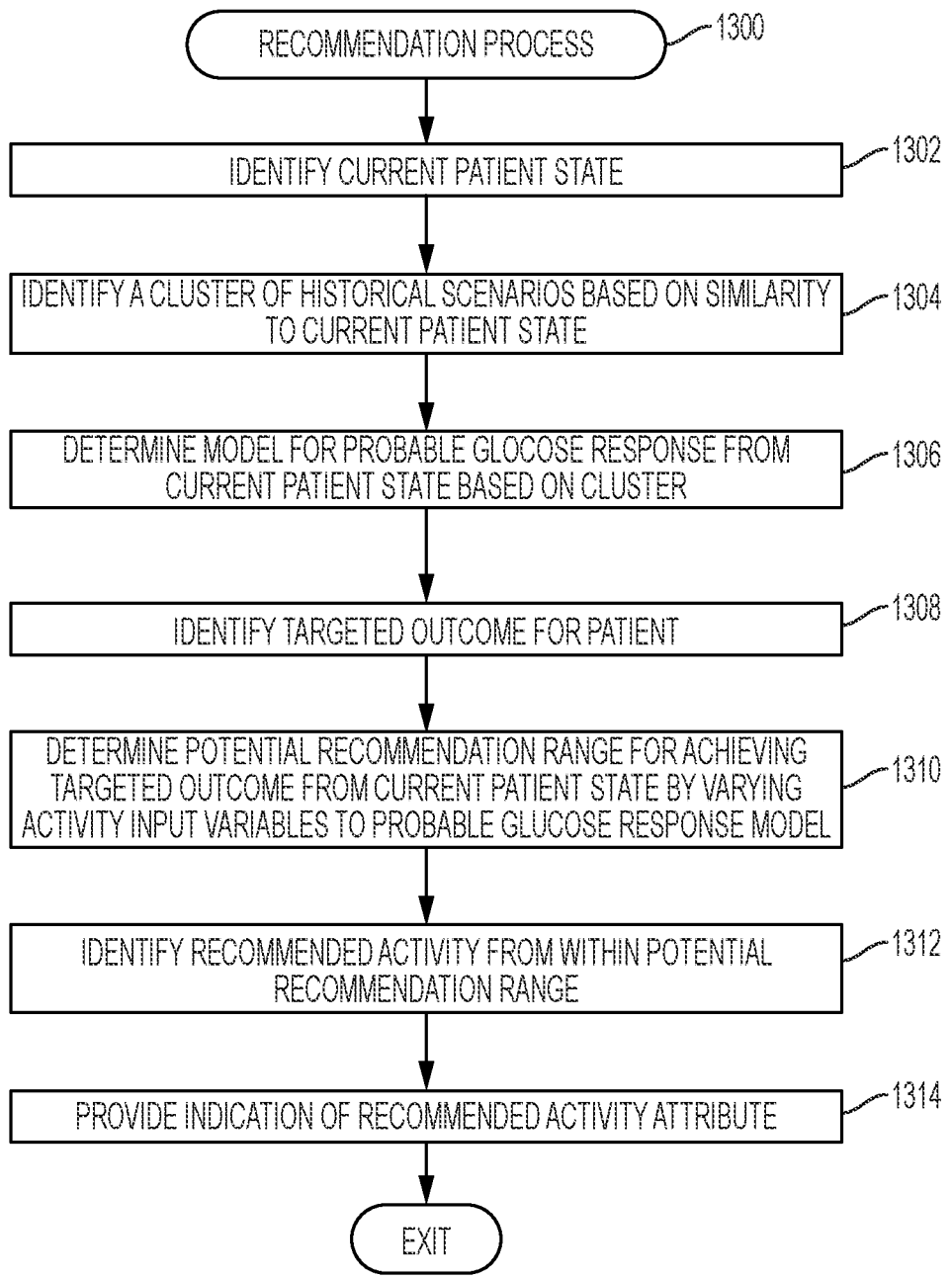
FIG. 13 is a flow diagram of an exemplary recommendation process suitable implementation in connection with a patient monitoring system in one or more exemplary embodiments.

FIG. 13 depicts an exemplary recommendation process 1300 suitable for implementation in an infusion system or other patient monitoring system to recommend activities or actions for a patient to engage in that are likely to achieve a desired outcome based on historical data. In this regard, as described in greater detail below, in some embodiments, the recommendation process 1300 may be performed in connection with the planning process 900 to recommend activities when creating an activity plan to achieve a desired physiological condition and/or in connection with the patient navigation process 1200 to recommend activities to compensate for deviations from the patient's preplanned physiological condition.

The various tasks performed in connection with the recommendation process 1300 may be performed by hardware, firmware, software executed by processing circuitry, or any combination thereof. For illustrative purposes, the following description refers to elements mentioned above in connection with FIGS. 1-8. In practice, portions of the recommendation process 1300 may be performed by different elements of an infusion system, such as, for example, an infusion device 102, 200, 502, 802, a client computing device 106, 806, a remote computing device 108, 814, and/or a pump control system 520, 600. It should be appreciated that the recommendation process 1300 may include any number of additional or alternative tasks, the tasks need not be performed in the illustrated order and/or the tasks may be performed concurrently, and/or the recommendation process 1300 may be incorporated into a more comprehensive procedure or process having additional functionality not described in detail herein. Moreover, one or more of the tasks shown and described in the context of FIG. 13 could be omitted from a practical embodiment of the recommendation process 1300 as long as the intended overall functionality remains intact.

In the illustrated embodiment, the recommendation process 1300 initializes or otherwise begins by identifying the current operational context or state of the patient at the time associated with the recommendation (task 1302). For example, for real-time recommendations, the client application 808 at the client device 806 may retrieve or otherwise obtain, either from local memory at the client device 806, the database 816 and/or other devices 802, 804, 814 in the patient monitoring system 800, current or recent measurement data characterizing the current physiological state of the patient (e.g., glucose measurement data, heart rate measurement data, and/or other auxiliary measurement data) along with insulin delivery data, insulin on board data, meal data, exercise event data, geographic location data, and/or other data characterizing the current operational context.

The recommendation process 1300 continues by identifying a cluster of historical patient states corresponding to the current patient state (task 1304). In this regard, the recommendation process 1300 analyzes historical patient data in the database 816 to identify previous situations where a bolus, meal, exercise or other activity or event occurred having associated historical data that is substantially similar to the current patient state or operational context. A nearest neighbor algorithm or similar machine learning technique may be performed to identify substantially similar historical situations multidimensionally. If sufficient data associated with the current patient of interest exists in the database 816, the cluster (or subset) of historical patient states are identified from within that patient's historical data. On the other hand, for a patient having insufficient historical data, a cluster of historical patient states may be identified from among historical data associated with substantially similar patients.

By way of example, in one embodiment, patient-specific demographic and/or physiological factors are utilized to map a patient to a patient population cluster that represents a subset of all patients having associated data maintained in the database 816. For example, if a plurality of different patient population clusters has been previously created or defined, the current patient may be mapped to a respective one of the existing patient population clusters based on the shortest Euclidean distance (in multidimensional space) from the patient's associated demographic and/or physiological information and the centroid of the respective patient population clusters.

Similarly, the patient's current state or operational context may be mapped to a cluster of historical scenarios within the historical data set being utilized to generate recommendations for the patient, which depending on the amount of available historical data may consist solely of that individual's historical data and/or historical data associated with other patients in the patient population cluster that the current patient was mapped to. For example, if the patient's current state corresponds to a meal event in the morning followed by 30 minutes of low intensity exercise, a corresponding cluster of historical scenarios involving a similar combination of a meal event and an exercise event may be identified within the historical data based on similarities between the time of day associated with the meal event for the current patient state and the respective times of day associated with the respective historical meal events, the amount of carbohydrates associated with the meal event for the current patient state and the respective amounts of carbohydrates associated with the respective historical meal events, the time of day associated with the exercise event for the current patient state and the respective times of day associated with the respective historical exercise events, the duration associated with the exercise event for the current patient state and the respective durations associated with the respective historical exercise events, the intensity associated with the exercise event for the current patient state and the respective intensity associated with the respective historical exercise events, and/or the like. Additionally, the current or recent glucose measurement data for the patient and/or other data characterizing the current patient state may be utilized to further refine the cluster of historical scenarios utilized for analysis. In some embodiments, a plurality of different clusters of the historical data corresponding to different patient states or scenarios may be created, with the current patient state being mapped to a respective one of the historical scenario clusters based on the shortest Euclidean distance from the current patient state the centroid of the respective historical scenario clusters.

For example, in one embodiment, a k-nearest neighbor algorithm may be utilized to utilized to map a patient to a patient population cluster. In this regard, the distance (D) between nearest neighbors in a patient population cluster may be calculated using the equation $$D = \frac{\sum_{1}^{n} K_{P_n} d_{P_n}}{\sum_{1}^{n} K_{P_n}},$$

where $P_n$ represents a respective parameter of interest ($P_n$) (e.g., insulin sensitivity factor, insulin-to-carbohydrate ratio, sensor glucose value at the time of bolusing, sensor glucose rate of change at the time of bolusing, etc.), $d_{P_n}$ represents the distance between the current patient's value for a respective parameter of interest and the representative value for that parameter of interest for the patient population cluster (e.g., the geometric mean of the patient population cluster), and $K_{P_n}$ represent weightings for the respective parameter of interest calculated using a kernel function. For example, a Gaussian kernel may be utilized to calculate weights for each parameter of interest as a function of the standard deviation of the patient's historical values for the respective parameter of interest. It should be noted that the parameters of interest utilized to cluster patients and/or the relative weightings associated therewith may be determined based on the predictive value of those parameters with respect to forecasting the glucose outcome. The current patient may be classified to a patient population cluster that results in a minimum value for the distance (D).

Still referring to FIG. 13, the recommendation process 1300 continues by creating or otherwise determining one or more models for predicting the patient's probable glucose response from the current patient state based on the cluster of historical scenarios mapped to the current patient state (task 1306). In this regard, the historical meal data, historical sensor glucose measurement data, historical insulin delivery data, historical auxiliary measurement data, historical geographic location data, and any other historical data associated with the historical scenarios is analyzed using machine learning to identify or otherwise determine the subset of the historical data that is predictive of or correlative to the subsequent glucose outcome. A corresponding equation or model for calculating a probable glucose response at one or more times after patient state at the recommendation time based on that subset of input variables may be determined, thereby characterizing or mapping a particular combination of values or attributes for the current patient state or operational context to a corresponding glucose response or outcome.

The recommendation process 1300 continues by identifying or otherwise determining a target glucose outcome for the patient and varying one or more input variables to the glucose prediction model(s) associated with the current patient state to identify a range of potential input variables capable of achieving the target glucose outcome (task 1308, 1310). In this manner, after calculating, determining, or otherwise developing a model for predicting the patient's probable glucose response from the current patient state, a solution space defining the potential recommendation range for one or more variables input to the model that will achieve the desired outcome may be determined. For example, continuing the above example, given the patient's current sensor glucose measurement data, the patient's current insulin on board, and the patient's current state corresponds to a meal event in the morning followed by 30 minutes of low intensity exercise, the vary an insulin bolus amount input to the probable glucose response model (e.g., from 0 to an upper limit or maximum value) and identify the range of input insulin bolus amount values that result in the probable glucose response model outputting a predicted glucose value that is within a desired target range for the patient (e.g., between 70 mg/dL and 170 mg/dL). It should be noted that the subject matter described herein is not limited to an individual variable input to the model, and may be implemented in an equivalent manner by varying multiple different input variables (e.g., bolus variables, meal variables, exercise variables, and the like) in concert to identify a multidimensional solution space that defines potential combinations of variable values that achieve the desired outcome (e.g., a combination of a bolus amount and an exercise duration, or the like).

After identifying a range or solution space for potential recommendations, in exemplary embodiments, the recommendation process 1300 selects or otherwise identifies a recommended value for an activity variable (or combination thereof) that achieves the targeted outcome from within the potential recommendation range and generates or otherwise provides indication notifying the patient or another user of the recommended activity attribute(s) (tasks 1312, 1314). In this regard, an optimal recommendation may be identified or otherwise selected from within the potential recommendation range in accordance with any number of optimization or selection criteria. For example, in one embodiment, to conserve insulin, a minimum insulin bolus amount or a combination of variables involving the minimum insulin bolus amount from within the recommendation solution space may be selected. In another embodiment, the potential solution for achieving the target outcome with the minimum amount of exercise or carbohydrates may be selected. In this regard, as described in greater detail below in the context of FIG. 14, in some embodiments, the recommended activity and recommended attributes associated therewith may be influenced by environmental context associated with the patient. For example, if inclement weather or other factors may deter, limit or otherwise influence the patient's ability to exercise, the model input variable solution that minimizes the amount of exercise required for achieving the targeted outcome may be selected as the optimal recommendation. Similarly, if the geographic location of the patient suggests the patient's ability to consume additional carbohydrates may be limited (e.g., the patient is in a remote area or not in proximity to any restaurants, grocery stores, and/or the like), the model input variable solution that minimizes the amount of carbohydrates required for achieving the targeted outcome may be selected as the optimal recommendation. In yet other embodiments, the mean, median, or other statistical representation of the recommendation solution space may be selected or identified as the optimal recommendation. In another embodiment, the optimal recommendation may be identified as the point within the recommendation solution space that results in a predicted glucose level that is closest to a target glucose level utilized by a closed-loop glucose control scheme implemented by the infusion device 102, 502, 802.

In one or more embodiments, prior to identifying the recommended activity variables for the current patient state, one or more safety checks are performed to filter, reduce, or otherwise limit the recommendation solution space based on historical data. For example, if a particular point within the recommendation solution space matches or is substantially similar to a historical scenario that was followed by a hypoglycemic or hyperglycemic event within a threshold amount of time after that activity (or combination thereof), that particular point may be removed from the recommendation solution space or utilized as an upper or lower bound for filtered recommendation solution space that is a subset of the initial recommendation solution space.

Additionally, or alternatively, in some embodiments, one or more other glucose prediction or forecasting models are utilized to provide a safety check on the recommended activity variables or the recommendation solution space. For example, based on the current patient state variables and a recommended activity variable, one or more predicted glucose values for the patient may be calculated or otherwise determined using a patient-specific glucose forecasting model, a patient-specific physiological model, a patient-specific autoregressive integrated moving average (ARIMA) model, and/or the like. In this regard, the recommendation process 1300 may verify or otherwise confirm that any potential recommended activity variable values within the recommendation solution space are unlikely to result in a hypoglycemic event, a hyperglycemic event, or some other glucose excursion above or below a target range of glucose values for the patient. For example, if inputting a recommended insulin bolus amount into a patient-specific glucose prediction model along with the patient's current glucose measurement value, current insulin on board, and/or other current patient state variables results in a predicted glucose value at some point in the future that is outside of the patient's target glucose range or above or below a particular glucose threshold, that recommended insulin bolus amount may be excluded from the recommendation solution space or otherwise prevented from being recommended to the patient.

In some embodiments, other practical factors independent of safety concerns may also be utilized to filter, limit, or otherwise refine the recommendation solution space. For example, the amount of insulin currently available in a reservoir of an infusion device 102, 502, 802 may be utilized as an upper limit on the potential insulin bolus amount variable value. Similarly, a remaining duration of time between the current time of day and an anticipated bedtime for the patient may be utilized as an upper limit on the potential exercise amount variable value.

Still referring to FIG. 13, and with continued reference to FIGS. 8-12, depending on the embodiment, the recommendation process 1300 may be performed prospectively in connection with the planning process 900 of FIG. 9 or in real-time in connection with the patient navigation process 1200 of FIG. 12. For example, in the context of the planning process 900, the recommendation process 1300 may be performed in connection with the predicted patient states at any time interval where a meal, bolus, exercise, or other activity is determined likely to occur. Additionally or alternatively, the recommendation process 1300 may be performed in connection with the predicted patient states at any time interval where the forecasted glucose level for the patient is above or below a threshold value (e.g., above a hyperglycemic event threshold or below a hypoglycemic event threshold) or where the forecasted glucose level is predicted to be outside of the desired target range for the patient. For example, referring to FIG. 10, in response to determining the predicted meal event for the patient involving 99 carbohydrates at 1 PM, the recommendation process 1300 may be performed to identify a cluster of historical scenarios involving a meal event of around 99 carbohydrates at around 1 PM and determine a model for the probable glucose response based on the historical scenarios. The probable glucose response model may be utilized to calculate probable glucose outcomes for the patient based on a current patient measurement value at the recommendation time equal to the forecasted glucose level at 1 PM (e.g., 130 mg/dL) and the predicted amount of carbohydrates while varying the bolus amount input variable to the probable glucose response model from 0 up to an upper limit (e.g., the historical maximum bolus size ever administered for the patient, the maximum amount of insulin available in the reservoir of the infusion device 802, etc.). In response to identifying a bolus amount of 10 units as the minimum amount of insulin bolus amount input to the probable glucose response model that results in a probable glucose outcome within the target range (e.g., the minimum insulin bolus for maintaining a probable postprandial glucose level below 170 mg/dL), the recommendation process 1300 may cause the client application 808 to automatically generate the planning GUI display 1100 with the bolus event slider 1030 initially configured to indicate 10 units of insulin at 1 PM initially in lieu of presenting the GUI display 1000 of FIG. 10 upon initialization of the planning process 900 that incorporates the recommendation process 1300.

As another example, in response to identifying the initially forecasted glucose level for the patient at 4 PM that is above the upper limit of the target range 1006, the recommendation process 1300 may be performed to identify a cluster of historical scenarios involving a meal event of around 99 carbohydrates in the afternoon and approximately 3 hours before a hyperglycemic glucose excursion, and then determine a model for the probable glucose response based on that cluster of historical scenarios. The probable glucose response model may then be utilized to calculate probable glucose outcomes for the patient based on a current patient measurement value at the recommendation time equal to the forecasted glucose level at 4 PM (e.g., 200 mg/dL) while varying the bolus amount input variable and/or exercise variables (e.g., duration and/or intensity) to the probable glucose response model to identify a recommended correction bolus amount, a recommended exercise event, and/or a combination thereof that the patient should perform at 4 PM to mitigate the hyperglycemic glucose excursion and more quickly restore the forecasted glucose levels to the target range. Thereafter, the recommendation process 1300 may cause the client application 808 to automatically generate a planning GUI display that indicates the recommended insulin bolus amount and/or exercise at 4 PM and the updated forecast glucose values for the 4 PM time interval and subsequent intervals accounting for the recommended activity initially in lieu of presenting the GUI display 1000 of FIG. 10 upon initialization of the planning process 900.

Additionally, or alternatively, the recommendation process 1300 is performed in real-time in concert with the patient navigation process 1200 of FIG. 12 to provide real-time recommendations to minimize deviations from the patient's originally forecasted glucose values. For example, when the patient's current glucose measurement value deviates from the originally forecasted glucose value for the current time interval by more than a threshold amount, the recommendation process 1300 may be initiated to generate a recommendation for best restoring the patient's glucose levels to the originally forecasted values. Based on the current patient state or operational context at the time of the deviation, a cluster of historical scenarios similar to the current state may be identified and utilized to create a model for the patient's probable glucose response. The activity input variables to the probable glucose response model may then be varied to identify a recommendation solution space that achieves a targeted glucose outcome. From within the recommendation solution space, the optimal activity input variable value (or combination thereof) may be identified that achieves a probable glucose response that minimizes the cumulative deviations from the originally forecasted glucose values going forward. For example, the recommended solution space may be analyzed using the patient's specific forecasting models, physiological models, ARIMA models, and/or the like to identify the optimal solution for patient activities that achieves the minimum amount of deviation from the patient's originally forecasted glucose values. The identified solution may then be provided to the patient, thereby indicating to the patient the recommended activity (or combination thereof) that is most likely to best restore the patient's glycemic condition to the originally planned glycemic condition going forward.

It should be noted that the recommendation process 1300 can be implemented and utilized in any number of different ways to recommend any number of different activities or actions that may influence the physiological condition of a patient, and moreover, can be done in concert with or independently of the planning process 900 and/or the navigation process 1200. Accordingly, the recommendation process 1300 should not be construed as being limited to any particular type of activity being recommended or limited to use in connection with the planning process 900 and/or the navigation process 1200. Additionally, it should be noted that in some embodiments the recommendation process 1300 may identify and concurrently provide multiple different recommendations from within the recommendation solution space, thereby providing the patient with a number of potential options to choose from. For example, the recommendation process 1300 may provide indication of a first recommendation that corresponds to a point within the recommendation solution space requiring the minimum amount of insulin, an indication of a second recommendation that corresponds to a point within the recommendation solution space requiring the mean or median amount of insulin, and an indication of a third recommendation that corresponds to a point within the recommendation solution space that achieves an optimal outcome (e.g., by minimizing the difference between the predicted glucose response and the targeted outcome).

In one or more embodiments, the recommendation process 1300 is manually initiated by the patient or other user of a client device 806 to request or otherwise obtain recommendations to achieve a desired glucose outcome. For example, the patient may interact with and utilize the client application 808 to obtain recommendations for activities to be performed by the patient before going to bed to help control or manage the patient's glucose levels when the patient wakes from sleep. In this regard, the patient's activities or events from the preceding day (e.g., since termination of a preceding overnight period or sleep event) may be utilized to identify a cluster of previous days similar to the patient's most recent day of activities. The historical data associated with those preceding days may be utilized to determine a model for predicting a glucose response at a wakeup time the following morning. The patient's current and recent data for the preceding time periods of the current day are input to the model along with estimations of the start and end times for the anticipated sleep period, which may be input by the patient or determined based on historical sleep events. An insulin bolus amount, carbohydrate amount, and exercise duration, and/or the like input to the wake-up glucose response model may be varied to identify a recommendation solution space for achieving a desired glucose level (or a range thereof) upon wake-up, which, in turn may be utilized to recommend one or more activities to the patient to achieve a desired glucose level upon waking.

It should be noted that in some embodiments, the recommendation process 1300 may utilize multiple different models for defining a recommendation solution space that accounts for multiple objectives. For example, machine learning may be applied to a cluster of historical scenarios to generate one or more models for predicting a probable glucose level (or range thereof) in addition to one or more models for predicting a probability of a hypoglycemic event, a hyperglycemic event, and/or other events. Varying activity input variables to each of the models may be done to identify, for each model, a respective recommendation solution space that achieves a desired glucose level (or range thereof), a desired probability (or range thereof) for an adverse glucose excursion event, and/or the like. The common overlapping portions of the recommendation solution spaces (e.g., the intersection of the recommendation solution spaces) may then be utilized to identify an optimal recommendation within the common recommendation solution space. In this manner, a recommendation may be provided that not only achieves a desired glucose outcome or level while also minimizing the likelihood of adverse glucose events. For example, the common overlapping portions of the recommendation solution spaces for achieving a glucose outcome within a target range, achieving a probability of a hypoglycemic event below a desired probability, and achieving a probability of a hyperglycemic event below a desired probability may be utilized to identify a recommended activity for the patient to achieve a desired wake-up glucose level while minimizing the probability of hypoglycemic or hyperglycemic events overnight.

As another example, the recommendation process 1300 may be utilized to provide recommendations for activities be performed by the patient before exercising to help control or manage the patient's glucose levels after exercise. In this regard, exercise plays a significant impact on the glucose levels of diabetes patients, who often find it challenging to balance carbohydrate intake, duration of exercise, and type of exercise. The model(s) utilized by the recommendation process 1300 may consider preceding carbohydrate intake and the prospective duration and type of exercise and provide recommendations for managing his or her glucose levels after exercise and/or provide recommendations pertaining to the amount carbohydrate intake, duration of exercise, and type of exercise the patient should engage in. For example, a first model may be created for predicting the post-exercise glucose level based on the duration of exercise, a second model may be created for predicting the post-exercise glucose level based on the duration of exercise and carbohydrate intake, a third model may be created for predicting the post-exercise glucose level based on the exercise duration and peak intensity of the exercise, and a fourth model may be created for predicting the post-exercise glucose level based on the exercise duration, peak exercise intensity, and carbohydrate intake. Neural networks, linear regression, or other machine learning techniques may be utilized to train the models for predicting post-exercise glucose levels as a function of one or more of the current sensor glucose measurement value at the exercise start time, the current rate of change in the sensor glucose measurements, the current time of day, the exercise duration variable (s), the exercise intensity variable(s) (e.g., percentage of time a peak intensity, percentage of time in fat burning zone, a percentage of time in an aerobic zone (or cardio), etc.), and/or the carbohydrate intake.

In an exemplary embodiment, the four different post-exercise glucose models are utilized to provide four different recommendations that may be provided to the patient at the start of exercise. For example, "if you exercise for 20 minutes, your post exercise glucose level will be around 100 mg/dL," "if you exercise for 30 minutes and have a snack with 15 grams of carbohydrates, your post exercise glucose level will be around 130 mg/dL," "if you work out for 40 minutes with 15 minutes in peak zone, 15 minutes in cardio zone and 10 minutes in fat burning zone, your post exercise glucose level will be 90 mg/dL," "if you work out for 40 minutes with 15 minutes in peak zone, 15 minutes in cardio zone and 10 minutes in fat burn zone and have a snack with 10 grams of carbohydrates, your post exercise glucose level will be 100 mg/dL." In this regard, the provided recommendations may correspond to the optimal recommendation identified from within the recommendation solution space for each respective model. In yet other embodiments, the optimal recommendations identified from within the recommendation solution spaces for each respective model may be averaged or otherwise combined to arrive at an aggregate recommendation.

It should be noted that by leveraging clusters of historical data for similar situations, adherence to the recommendation process 1300 may lead to improved patient outcomes relative to other approaches that rely on patient-specific factors with high variability, such as insulin sensitivity factors, carbohydrate ratios, and the like. In this regard, previously unidentifiable combined effects of various combinations of input variables may be identified or otherwise discerned and utilized to improve recommendations that reflect the current combination of variables, as compared to manually experimenting with different input variables, which can be time consuming, error prone, and exhibit lag as the patient's physiology evolves.

Recommendations Using Environmental Context

Figure 14:
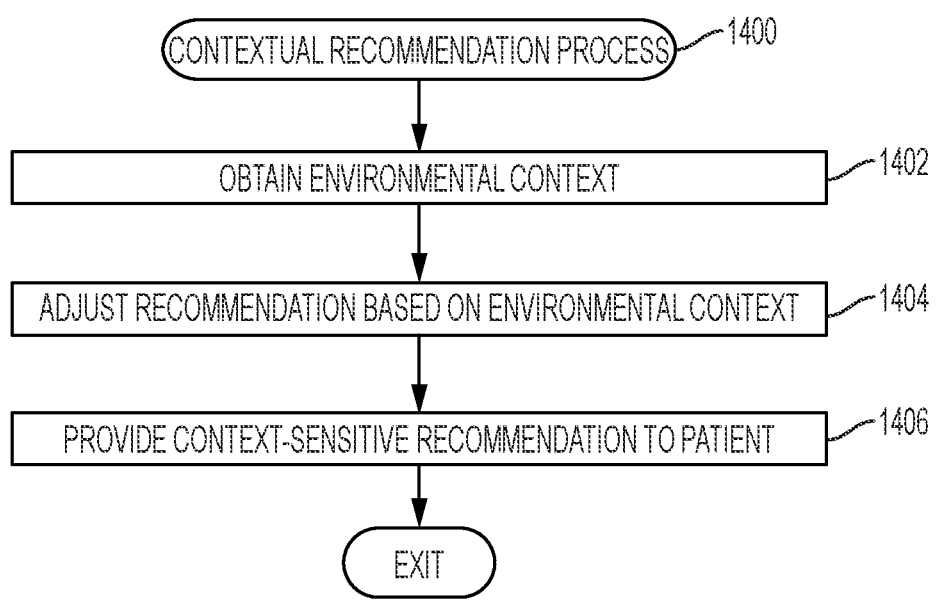
FIG. 14 is a flow diagram of an exemplary contextual recommendation process suitable implementation in connection with a patient monitoring system in one or more exemplary embodiments.

FIG. 14 depicts an exemplary contextual recommendation process 1400 suitable for implementation in an infusion system or other patient monitoring system to provide guidance for managing the physiological condition of a patient in a manner that is influenced by the contemporaneous environmental context. The various tasks performed in connection with the contextual recommendation process 1400 may be performed by hardware, firmware, software executed by processing circuitry, or any combination thereof. For illustrative purposes, the following description refers to elements mentioned above in connection with FIGS. 1-8. In practice, portions of the contextual recommendation process 1400 may be performed by different elements of an infusion system, such as, for example, an infusion device 102, 200, 502, 802, a client computing device 106, 806, a remote computing device 108, 814, and/or a pump control system 520, 600. It should be appreciated that the contextual recommendation process 1400 may include any number of additional or alternative tasks, the tasks need not be performed in the illustrated order and/or the tasks may be performed concurrently, and/or the contextual recommendation process 1400 may be incorporated into a more comprehensive procedure or process having additional functionality not described in detail herein. Moreover, one or more of the tasks shown and described in the context of FIG. 14 could be omitted from a practical embodiment of the contextual recommendation process 1400 as long as the intended overall functionality remains intact.

The illustrated contextual recommendation process 1400 receives or otherwise obtains environmental context information contemporaneous to a recommendation to be provided, adjusts or otherwise modifies the recommendation in a manner that is influenced by the environmental context information, and generates or otherwise provides a context-sensitive recommendation to the patient (tasks 1402, 1404, 1406). In this regard, the contextual recommendation process 1400 is performed to adjust or modify recommendations provided to a patient in a manner that is influenced by the contemporaneous geographic location, meteorological conditions, and/or other contemporaneous environmental contexts. In the context of a real-time recommendation, the client application 808 at the client device 806 may obtain from one or more sensing arrangements of the client device 806 and/or other sensing arrangements 506, 550, 560 environmental context data, such as, for example, the current geographic location of the patient and the current temperature, humidity, and/or other measurement data pertaining to the patient's current environment. Additionally, or alternatively, in some embodiments, the client application 808 at the client device 806 may also obtain environmental context data from another device via the network 812, for example, by querying a meteorological system or service using the current geographic location of the patient to obtain the current and/or forecasted meteorological conditions at the patient's location.

In one or more embodiments, the environmental context data is utilized to adjust or otherwise modify the recommended activities identified for the patient. For example, as described above in the context of the recommendation process 1300 of FIG. 13, in some embodiments, the environmental context data may be utilized to influence the recommendation identified from within the recommendation solution space (e.g., at task 1312). In this regard, the geographic location, meteorological conditions, or other environmental context may be factored into the optimization or selection scheme(s) utilized to identify recommended activities (and attributes thereof). For example, if the current geographic location corresponds to a remote location away from potential sources of carbohydrates, the recommendation process 1300 may be adjusted to select or identify a recommendation having a minimum amount of carbohydrates associated therewith (e.g., by minimizing a meal attribute input variable to a model). As another example, if the current meteorological conditions are inclement or otherwise likely to discourage the patient from exercising, the recommendation process 1300 may be adjusted to select or identify a recommendation having a minimum amount of exercise associated therewith (e.g., by minimizing an exercise attribute input variable to a model). As yet another example, if the amount of insulin available in a reservoir of the infusion device 102, 502, 802 is low or below a threshold and the current geographic location is not within a threshold distance of a pharmacy, the patient's home, or other potential sources of additional insulin, the recommendation process 1300 may be adjusted to select or identify a recommendation having a minimum amount of insulin associated therewith (e.g., by minimizing a bolus attribute input variable to a model). In this regard, in various embodiments, the geographic location and meteorological conditions may be utilized in combination to result in the recommendation process 1300 identifying a recommendation optimized for the patient's current environment.

In one or more embodiments, the geographic location is utilized to supplement or enhance the recommendation provided to the patient, for example, by querying another device or resource on the network 812 to identify potential locations near the patient's geographic location that may be of use in achieving the recommended activity. For example, if the recommendation entails consuming carbohydrates, the current geographic location may be utilized to query for restaurants, grocery stores, or other potential locations where food may be available and provide indicia of one or more nearby sources of food in connection with the recommendation provided to the patient. Similarly, if the recommendation involves the patient engaging in exercise, the current geographic location may be utilized to query for gyms, fitness centers, recreation areas, or other locations suitable for the recommended type or duration of exercise and provide indicia of those locations to the patient in connection with the exercise recommendation. Various other factors, such as preexisting affiliations or associations with the patient, a manufacturer of a respective device 802, 806, and/or the like, may be utilized to filter or otherwise select recommended locations from within a set of nearby locations for the patient's current geographic location.

It should be noted that the contextual recommendation process 1400 is not limited to use with the recommendation process 1300 and may be performed in connection with any other sort of recommendation scheme or algorithm. For example, the contextual recommendation process 1400 may be initiated when the patient's glucose level in the future (e.g., in 30 minutes) is predicted to fall below a threshold value based on the patient's current glucose measurement value, the patient's recent glucose measurement values, a trend in the patient's glucose measurement values, and/or an amount of active insulin on board that is yet to be metabolized by the patient. Based on the predicted glucose level and/or the current insulin on board, an estimated amount of carbohydrates may be determined for mitigating potential hypoglycemia using any number of known techniques. The contextual recommendation process 1400 may then be performed using the current geographic location to identify potential nearby locations or services capable of providing the estimated amount of carbohydrates. For example, the client application 808 may utilize an application program interface (API) to provide the current geographic location and potentially other attributes pertaining to the recommendation (e.g., the recommended amount of carbohydrates, the type of food being recommended) to a server or other device on the network 812 that is configured to respond to the API request by querying a database using the information provided with the request and returning a list of services that match the recommendation information (e.g., the recommended amount of carbohydrates, the type of food being recommended) and are ranked or ordered based on relative distance from the current geographic location of the patient. Thus, when the patient's predicted glucose level in 30 minutes is expected to fall below a hypoglycemic alerting threshold (e.g., 70 mg/dL), the contextual recommendation process 1400 may be performed to provide a listing of nearby locations where the patient could satisfy, accomplish, or otherwise achieve the recommended activity. In some embodiments, the client application 808 may be configurable to allow the patient to select or otherwise identify a nearby service from the list, which, in turn results in another application or API request being initiated that results in directions to the selected service being provided via the client device 806.

As another example, the contextual recommendation process 1400 may be initiated when the patient's glucose level is predicted to rise above a hyperglycemic threshold value (e.g., 240 mg/dL) based on the patient's current glucose measurement value, the patient's recent glucose measurement values, a trend in the patient's glucose measurement values, etc. The contextual recommendation process 1400 may then be performed using the current geographic location to tailor an exercise recommendation to the patient's current location. For example, if the current geographic location is within a threshold distance of a gym, fitness center, or other exercise location associated with the patient (which may be identified based on the patient's historical data), the contextual recommendation process 1400 may provide a recommendation that the patient go to that location to engage in a particular type and/or duration of exercise. In this regard, some embodiments may also utilize an API to obtain and provide directions to the recommended location for the exercise in connection with recommending the type and duration or exercise. Conversely, if the patient's current geographic location is near his or her home, the contextual recommendation process 1400 may provide a recommendation that the patient go for a walk around the block or to a nearby park, recreation area, or the like for the recommended duration of time. As another example, the patient's current geographic location may be utilized to identify a nearby a point of interest and having a distance from the patient's current geographic location that generally corresponds to the recommended exercise duration based on the patient's typical walking speed. In such embodiments, the patient may be provided with an identification of the point of interest that it is suggested the patient walk to along with directions for walking to the point of interest.

It should be noted that the contextual recommendation process 1400 may also be utilized to provide multiple different recommendations for potential activities concurrently. For example, a recommendation to go perform a particular type of exercise at a nearby gym could be provided concurrently with a recommendation to walk to a point of interest or other exercise recommendations appropriate given the patient's current geographic location and/or the current meteorological conditions. Thus, the patient may select the patient's preferred activity from a list of recommended potential activities that are relevant or tailored to the patient's current geographic location and/or the current meteorological conditions. In some embodiments, the contextual recommendation process 1400 may utilize the geographic location, meteorological conditions, and/or historical activity data associated with the patient to identify which of the recommended potential activities is most likely to be relevant to the current environmental context and preferentially display that recommended activity in the list of recommended potential activities (e.g., at the top of the list, as the leftmost item in the list, etc.).

Additionally, it should be noted that the contextual recommendation process 1400 may also be performed prospectively in connection with the planning process 900 or other planning activities being performed by the patient. For example, an anticipated or predicted geographic location at a particular point in time and/or forecasted meteorological conditions at a predicted geographic location at a particular point in time may be utilized to adjust or otherwise tailor the recommendations provided in connection with the planning process 900 or planning GUI displays 1000, 1100. In this regard, the patient may input or otherwise provide, to the client application 808, information detailing the various lifestyle events or activities that the patient is likely to engage in throughout the day, which, in turn, may be factored in to the recommendation process 1300 when generating or providing recommendations on a planning GUI display 1000, 1100. For example, a patient may indicate that he or she will likely be at school, work, or some other particular geographic location during periods of the day. A meteorological forecast for that geographic location over those periods of the day may be obtained (e.g., via the network 812), and then utilized in connection with the anticipated geographic location to provide context-sensitive recommendations during that period of the day when the patient is planning at being at that location. It should be noted that in some embodiments, the predicted geographic location at various times of day may be estimated or otherwise determined by the client application 808 based on the patient's associated historical data maintained in the database 816 (e.g., the patient tends to be at a particular location during particular times on a particular day of the week).

As another example, the contextual recommendation process 1400 may be implemented or otherwise performed in connection with a trip planning feature supported by the client application 808 (which could be integrated with or separate from day planning features). In such embodiments, the patient may input or otherwise provide the location where the patient intends to go. The recommendation engine of the client application 808 may obtain the current geographic location of the patient and utilize an API to obtain or otherwise determine an estimated duration of time for the upcoming travel. The patient's glucose levels may then be predicted or otherwise determined for the duration of the trip (e.g., using a patient-specific forecasting model, physiological model, ARIMA model, and/or the like). If the probability of the patient experiencing a hypoglycemic or hyperglycemic event during the trip given the current patient state is greater than a threshold risk tolerance, the contextual recommendation process 1400 may identify locations of nearby services along the planned route in advance of when the patient is expected to experience a hypoglycemic or hyperglycemic event and recommend one or more activities for the patient at one or more nearby services along the planned route. For example, the contextual recommendation process 1400 may suggest stores, restaurants, or other businesses or services along the planned route where the patient may be able to obtain food, insulin, medication, or the like or engage in exercise to manage his or her glucose levels while en route. The client application 808 may be configurable to allow a recommendation selected by the patient to be added to the planned route of travel as a stop along the route. In some embodiments, where travel or other situations where the patient's ability to remedy his or her condition may be limited for an extended duration of time, the recommendation engine may more aggressively attempt to avoid a hypoglycemic or hyperglycemic event during that duration of time, for example, by recommending the patient bring a glucose tablet, increase alert volume or modify other notification settings, and/or other actions in advance.

Bolus Recommendations with Cost Optimization

Figure 15:
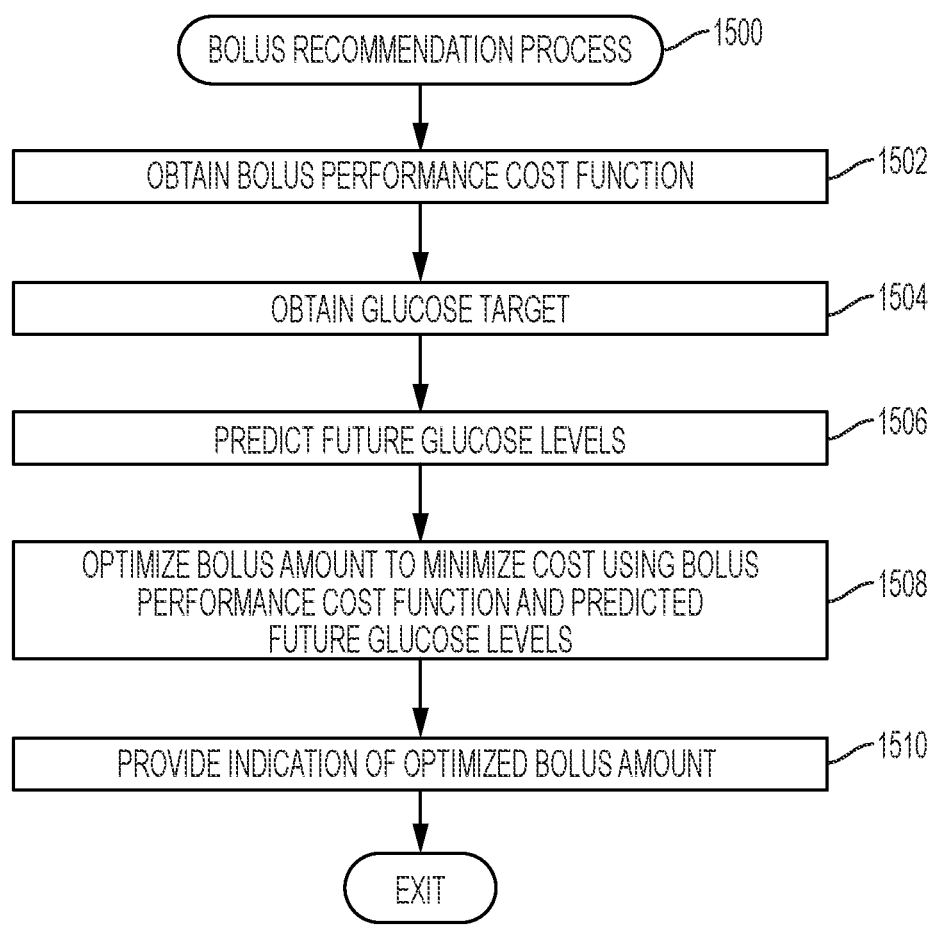
FIG. 15 is a flow diagram of an exemplary bolus recommendation process suitable implementation in connection with a patient monitoring system in one or more exemplary embodiments.

FIG. 15 depicts an exemplary bolus recommendation process 1500 suitable for implementation in an infusion system or other patient monitoring system to recommend an amount of fluid to be provided in a bolus. Depending on the embodiment, the bolus recommendation process 1500 may be performed in connection with any one of the processes 900, 1200, 1300, 1400 when an insulin bolus is indicated for managing a patient's glucose level, or independently whenever a patient attempts to manually administer an insulin bolus. The various tasks performed in connection with the bolus recommendation process 1500 may be performed by hardware, firmware, software executed by processing circuitry, or any combination thereof. For illustrative purposes, the following description refers to elements mentioned above in connection with FIGS. 1-8. In practice, portions of the bolus recommendation process 1500 may be performed by different elements of an infusion system, such as, for example, an infusion device 102, 200, 502, 802, a client computing device 106, 806, a remote computing device 108, 814, and/or a pump control system 520, 600. It should be appreciated that the bolus recommendation process 1500 may include any number of additional or alternative tasks, the tasks need not be performed in the illustrated order and/or the tasks may be performed concurrently, and/or the bolus recommendation process 1500 may be incorporated into a more comprehensive procedure or process having additional functionality not described in detail herein. Moreover, one or more of the tasks shown and described in the context of FIG. 15 could be omitted from a practical embodiment of the bolus recommendation process 1500 as long as the intended overall functionality remains intact.

Figure 16:
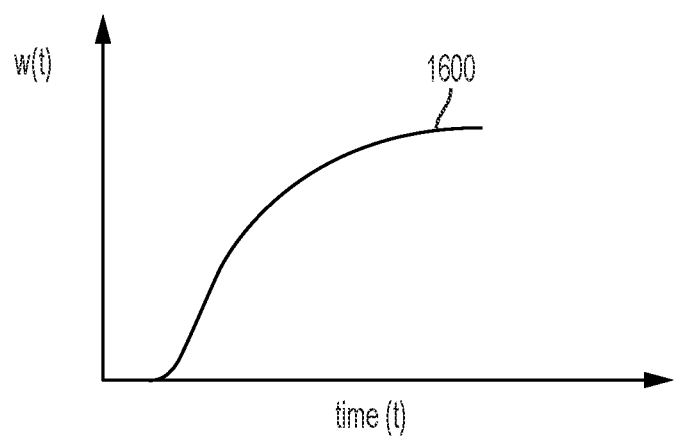
FIGS. 16-17 depict exemplary cost functions suitable for use in connection with one or more exemplary embodiments of the bolus recommendation process of FIG. 15.
Figure 17:
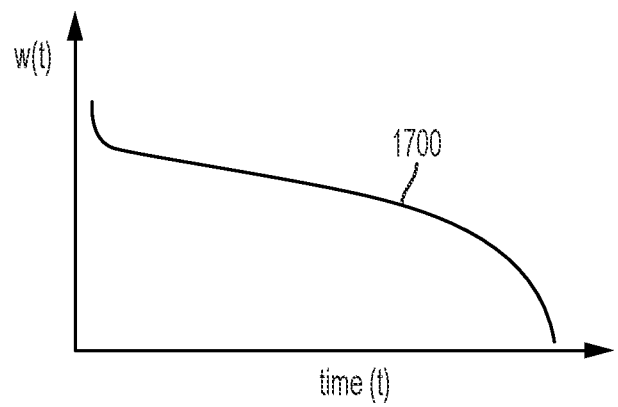

In exemplary embodiments, the bolus recommendation process 1500 initializes by identifying or otherwise obtaining a cost function representative of a desired performance to be achieved by the bolus (task 1502). In this regard, the cost function represents the relative weightings applied to differences between the patient's predicted glucose level and the patient's targeted level with respect to time, which may be configurable by the patient, the patient's healthcare provider, or any other user to achieve a desired temporal performance with respect to the patient's glucose levels. For example, FIG. 16 depicts a graphical representation 1600 of an example cost function with respect to time (w(t)) that increases the weighting applied to deviations further into the future relative to the current time associated with the bolus (e.g., at time t=0), thereby penalizing future deviations more heavily to better achieve a desired long-term bolus performance (e.g., to avoid a potential hypoglycemic condition after the insulin is fully metabolized). Conversely, FIG. 17 depicts a graphical representation 1700 of an example cost function with respect to time that decreases the weighting applied to deviations further into the future relative to the current time associated with the bolus, thereby penalizing immediate deviations most heavily to achieve a more immediate bolus response in the short-term (e.g., to avoid a hyperglycemic condition). In exemplary embodiments, the value of cost function is non-uniform with respect to time. The bolus performance cost function may be stored locally at a medical device 102, 502, 802 or other client device 808, or alternatively, may be stored at the remote database 816 and retrieved over the network 812 via the remote device 814. In one or more embodiments, the bolus performance cost function may be adjustable or otherwise configurable on a per-patient basis to achieve a patient-specific bolus performance. In yet other embodiments, bolus performance cost functions specific to a particular patient cluster or population may be utilized.

Still referring to FIG. 15, the bolus recommendation process 1500 continues by identifying or otherwise obtaining a glucose target for the patient (task 1504). In one embodiment, the glucose target corresponds to a reference or target glucose level utilized by a closed-loop control scheme implemented by an infusion device 102, 502, 802 to regulate the patient's glucose level to that reference glucose level. In another embodiment, the glucose target may correspond to a mean or midpoint of a target range of glucose values for the patient. In other embodiments, the glucose target value to be utilized for purposes of the bolus recommendation process 1500, may be input or otherwise provided by the patient or other user attempting to manually initiate a bolus (e.g., as part of a bolus wizard feature or other bolusing GUI display or application).

The bolus recommendation process 1500 calculates or otherwise predicts the patient's future glucose levels based on the patient state contemporaneous to the bolus recommendation using one or more glucose prediction models for the patient and adjusts, varies, or otherwise optimizes the insulin bolus amount input to the glucose prediction model(s) to minimize the total cost using the bolus performance cost function (tasks 1506, 1508). In this regard, the optimized insulin bolus amount achieves the desired performance of the insulin bolus with respect to a period of time corresponding to the duration of the cost function and in accordance with the relative weightings or costs prescribed by the cost function with respect to time. The optimized insulin bolus amount that minimizes the total cost corresponding to the deviation between the patient's future glucose levels and the patient's target glucose level is displayed or otherwise provided to the patient as the recommended insulin bolus amount (task 1510).

For example, a patient-specific forecasting model, a patient-specific physiological model, a patient-specific ARIMA model, or any other suitable glucose prediction model (or combination or ensemble thereof) may be utilize to calculate or otherwise predict the patient's future glucose levels at various points or times in the future based on the patient's current or recent glucose measurement data and other data characterizing the current state of the patient, such as is described above and in greater detail in U.S. patent application Ser. No. 15/933,264. In one or more exemplary embodiments, the predicted future glucose levels are determined at different sampling times in the future and for a duration of time into the future corresponding to the bolus performance cost function. For example, if the bolus performance cost function includes weighting factors at 5-minute intervals for a period of 4 hours in advance of the current time, predicted future glucose values may be calculated for the patient at 5-minute intervals spanning the next 4 hours.

Figure 18:
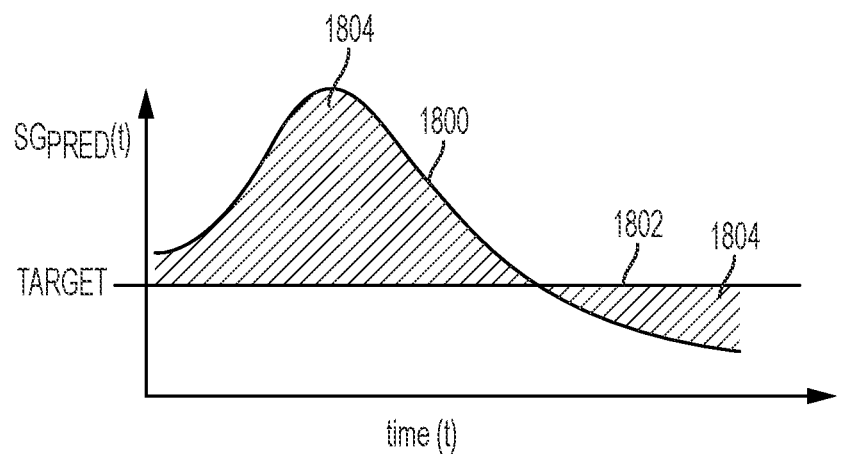
FIG. 18 depicts an exemplary graph of a prediction for a physiological condition of a patient with respect to a target value for the physiological condition of the patient that is suitable for use in connection with one or more exemplary embodiments of the bolus recommendation process of FIG. 15.

FIG. 18 depicts an exemplary graphical representation 1800 of a patient's predicted glucose values with respect to a graphical representation 1802 of the patient's target glucose value. The difference between each of the predicted future glucose values and the target glucose value is determined (represented by the shaded regions 1804), and the differences are multiplied by the corresponding weighting factors from the bolus performance cost function to achieve a total cost according to the bolus performance cost function. The insulin bolus amount input to the glucose prediction model(s) being utilized to calculate the predicted future glucose values is adjusted or varied throughout a range of potential values to identify the optimal insulin bolus amount that minimizes the total cost according to the bolus performance cost function. For example, the optimal insulin bolus amount (J) that minimizes the area between the patient's predicted future glucose values and the target glucose value may represented by the equation $J=\mathrm{argmin}(\Sigma w(t)(SG_{PRED}(t)-\mathrm{target})^2)$, where w(t) represents the bolus performance cost function with respect to time into the future, $SG_{PRED}(t)$ represents the predicted future glucose values with respect to time into the future, and target represented the target glucose value. In this regard, FIG. 18 may depict a predicted glucose level 1800 for a solution that optimizes the insulin bolus amount using a bolus performance cost function that increases the weighting factor with respect to time to minimize long-term deviations, such as the cost function 1600 depicted in FIG. 16. In embodiments where the glucose prediction models do not account for the active insulin on board that is yet to be metabolized, the recommended bolus amount may be determined by subtracting the amount of active insulin on board from the optimal insulin bolus amount.

In one or more embodiments, the bolus recommendation process 1500 may be implemented or otherwise performed in connection the planning process 900. For example, referring again to FIG. 10 and an exemplary case described above, in response to identifying a meal event at 1 PM or postprandial hyperglycemia at 4 PM, the bolus recommendation process 1500 may be performed to identify and recommend an optimal insulin bolus amount at the respective time on the planning GUI display 1000 (e.g., at 1 PM or 4 PM) that minimizes the cost associated with the deviation between the patient's subsequent forecast glucose levels and the patient's target glucose level. Similarly, the bolus recommendation process 1500 may be implemented or otherwise performed in connection the patient navigation process 1200. For example, if at 4 PM, the postprandial response in the patient's glucose level results in the patient's current glucose measurement value exceeding the forecasted glucose level for 4 PM by more than a threshold or otherwise exceeding the upper limit of the target range 1006 (e.g., 170 mg/dL), the client application 808 may perform the bolus recommendation process 1500 and provide a recommendation that the patient administer a correction bolus with an amount that is optimized to achieve a desired performance according to the bolus performance cost function for the patient. In this regard, in some embodiments, the patient's originally planned levels at the current and/or subsequent times of day may be utilized as the target glucose value (e.g., task 1504) when determining the optimal bolus amount.

It should be noted that the bolus recommendation process 1500 may be implemented or otherwise performed in connection the recommendation process 1300 of FIG. 13. In this regard, the bolus recommendation process 1500 may be performed to select or otherwise identify a recommended insulin bolus amount (e.g., at task 1312) from within a recommendation solution space. For example, the bolus recommendation process 1500 may adjust the insulin bolus amount input to the glucose prediction model(s) being utilized to calculate the predicted future glucose values throughout the range of potential values identified by the recommendation process 1300 (e.g., at task 1310) to identify the optimal insulin bolus amount that minimizes the total cost according to the bolus performance cost function from within the acceptable range of potential insulin bolus amounts.

The bolus recommendation process 1500 may also be implemented or otherwise performed in connection the contextual recommendation process 1400 of FIG. 14. In this regard, based on the patient's current or planned geographic locations, the bolus performance cost function for the patient may be selected, chosen, or adjusted to account to the relative availability of different services at different times of the day in the future. For example, if there is a period of time where the patient is expected to be in a remote location, the weighting factors of the bolus performance cost function for that period of time may be increased to more heavily penalize deviations during that time period where the patient may have a more limited ability to pursue the full range of remedial actions that may be otherwise available to the patient in other geographic locations.

It should be noted that the bolus recommendation process 1500 and related subject matter described herein is not limited to any particular cost function, and in practice, the cost function may vary depending on the therapy goals determined by a patient, physician, or other healthcare provider. In other embodiments, the cost function may be automatically determined based on historical patient data, either on a patient-specific basis or based on a particular patient population. For example, grid searching or other machine learning may be utilized to identify a cost function that is likely to achieve a desired optimization of glucose control with respect to time. Additionally, it should be noted that the bolus recommendation process 1500 is not limited to single boluses and may be implemented in an equivalent manner for multiple or split boluses, extended boluses, micro boluses, or any other bolusing scheme or sequence that utilizes multiple bolus deliveries (e.g., to account for a particular type of food being consumed). In this regard, the cost function may be utilized to optimize each of the individual boluses concurrently or in concert with one another prior to delivery or initialization of the bolus sequence to more accurately determine amounts for the individual boluses and achieve the desired performance of the bolus sequence over time.

Diabetes Data Management System Overview

Figure 19:
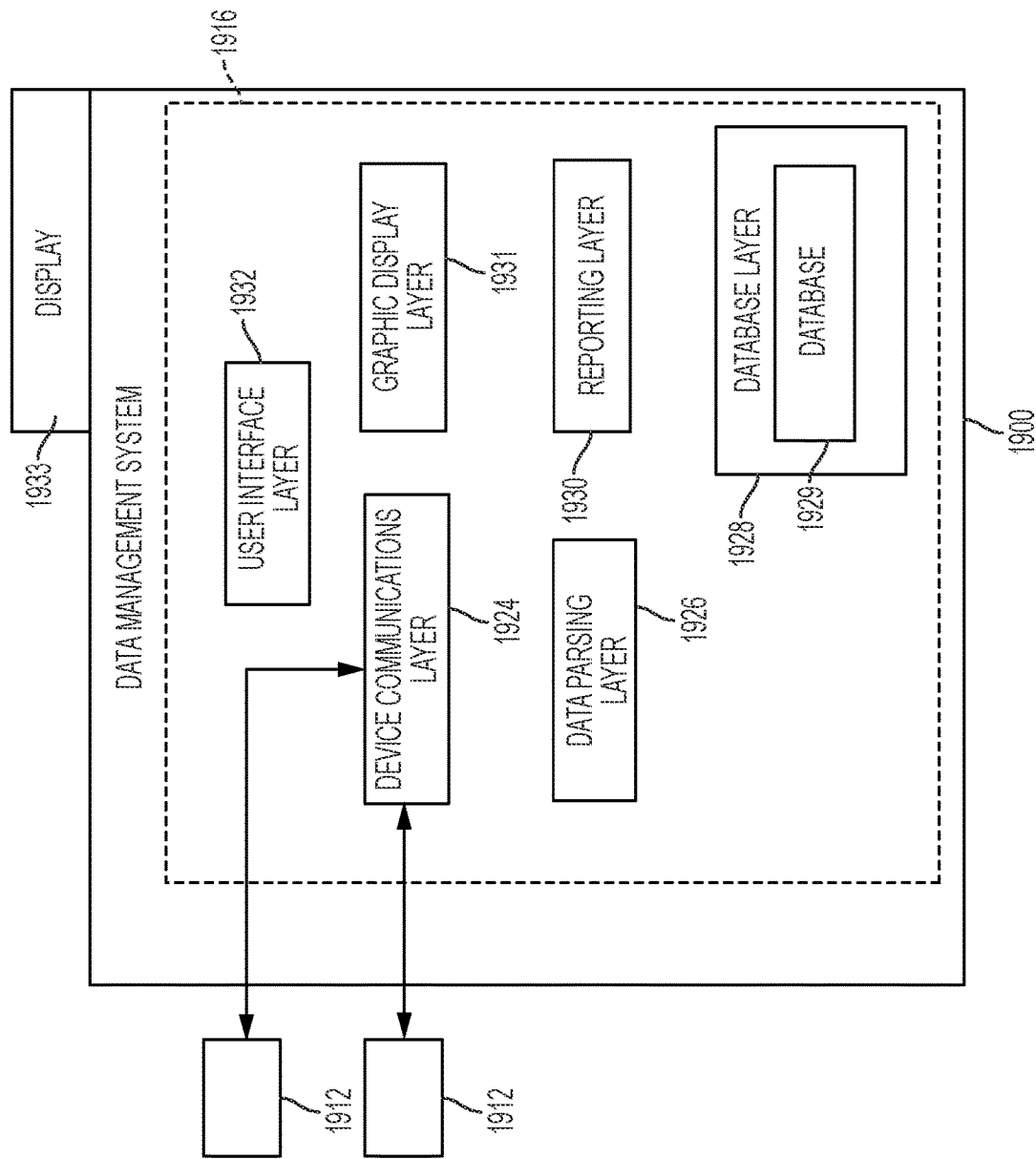
FIG. 19 depicts an embodiment of a computing device of a diabetes data management system suitable for use in connection with any one or more of the systems of FIGS. 1, 5 and 8 and any one or more of the processes of FIGS. 9 and 12-15 in accordance with one or more embodiments.

FIG. 19 illustrates a computing device 1900 suitable for use as part of a diabetes data management system in conjunction with one or more of the processes described above in the context of FIGS. 9-18. The diabetes data management system (DDMS) may be referred to as the Medtronic MiniMed CARELINK™ system or as a medical data management system (MDMS) in some embodiments. The DDMS may be housed on a server or a plurality of servers which a user or a health care professional may access via a communications network via the Internet or the World Wide Web. Some models of the DDMS, which is described as an MDMS, are described in U.S. Patent Application Publication Nos. 2006/0031094 and 2013/0338630, which is herein incorporated by reference in their entirety.

While description of embodiments is made in regard to monitoring medical or biological conditions for subjects having diabetes, the systems and processes herein are applicable to monitoring medical or biological conditions for cardiac subjects, cancer subjects, HIV subjects, subjects with other disease, infection, or controllable conditions, or various combinations thereof.

In embodiments of the invention, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 1900. The computing device 1900 may be coupled to a display 1933. In some embodiments, the computing device 1900 may be in a physical device separate from the display (such as in a personal computer, a mini-computer, etc.) In some embodiments, the computing device 1900 may be in a single physical enclosure or device with the display 1933 such as a laptop where the display 1933 is integrated into the computing device. In embodiments of the invention, the computing device 1900 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/glucose sensor having a display. The computing device may also be an insulin pump coupled to a display, a glucose meter coupled to a display, or a glucose sensor coupled to a display. The computing device 1900 may also be a server located on the Internet that is accessible via a browser installed on a laptop computer, desktop computer, a network computer, or a PDA. The computing device 1900 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 802.11 protocols.

In the embodiment shown in FIG. 19, the data management system 1916 comprises a group of interrelated software modules or layers that specialize in different tasks. The system software includes a device communication layer 1924, a data parsing layer 1926, a database layer 1928, database storage devices 1929, a reporting layer 1930, a graph display layer 1931, and a user interface layer 1932. The diabetes data management system may communicate with a plurality of subject support devices 1912, two of which are illustrated in FIG. 19. Although the different reference numerals refer to a number of layers, (e.g., a device communication layer, a data parsing layer, a database layer), each layer may include a single software module or a plurality of software modules. For example, the device communications layer 1924 may include a number of interacting software modules, libraries, etc. In embodiments of the invention, the data management system 1916 may be installed onto a non-volatile storage area (memory such as flash memory, hard disk, removable hard, DVD-RW, CD-RW) of the computing device 1900. If the data management system 1916 is selected or initiated, the system 1916 may be loaded into a volatile storage (memory such as DRAM, SRAM, RAM, DDRAM) for execution.

The device communication layer 1924 is responsible for interfacing with at least one, and, in further embodiments, to a plurality of different types of subject support devices 1912, such as, for example, blood glucose meters, glucose sensors/monitors, or an infusion pump. In one embodiment, the device communication layer 1924 may be configured to communicate with a single type of subject support device 1912. However, in more comprehensive embodiments, the device communication layer 1924 is configured to communicate with multiple different types of subject support devices 1912, such as devices made from multiple different manufacturers, multiple different models from a particular manufacturer and/or multiple different devices that provide different functions (such as infusion functions, sensing functions, metering functions, communication functions, user interface functions, or combinations thereof). By providing an ability to interface with multiple different types of subject support devices 1912, the diabetes data management system 1916 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 1924 allows the DDMS 1916 to receive information from and transmit information to or from each subject support device 1912 in the system 1916. Depending upon the embodiment and context of use, the type of information that may be communicated between the system 1916 and device 1912 may include, but is not limited to, data, programs, updated software, education materials, warning messages, notifications, device settings, therapy parameters, or the like. The device communication layer 1924 may include suitable routines for detecting the type of subject support device 1912 in communication with the system 1916 and implementing appropriate communication protocols for that type of device 1912. Alternatively, or in addition, the subject support device 1912 may communicate information in packets or other data arrangements, where the communication includes a preamble or other portion that includes device identification information for identifying the type of the subject support device. Alternatively, or in addition, the subject support device 1912 may include suitable user-operable interfaces for allowing a user to enter information (e.g., by selecting an optional icon or text or other device identifier) that corresponds to the type of subject support device used by that user. Such information may be communicated to the system 1916, through a network connection. In yet further embodiments, the system 1916 may detect the type of subject support device 1912 it is communicating with in the manner described above and then may send a message requiring the user to verify that the system 1916 properly detected the type of subject support device being used by the user. For systems 1916 that are capable of communicating with multiple different types of subject support devices 1912, the device communication layer 1924 may be capable of implementing multiple different communication protocols and selects a protocol that is appropriate for the detected type of subject support device.

The data-parsing layer 1926 is responsible for validating the integrity of device data received and for inputting it correctly into a database 1929. A cyclic redundancy check CRC process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 1916 may compare received identification information with pre-stored information to evaluate whether the received information is from a valid source.

The database layer 1928 may include a centralized database repository that is responsible for warehousing and archiving stored data in an organized format for later access, and retrieval. The database layer 1928 operates with one or more data storage device(s) 1929 suitable for storing and providing access to data in the manner described herein. Such data storage device(s) 1929 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. Information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 1916 or other entities, for analyzing group data or other forms of conglomerate data.

Embodiments of the database layer 1928 and other components of the system 1916 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 1928 may be configured to limit access of each user to types of information pre-authorized for that user. For example, a subject may be allowed access to his or her individual medical information (with individual identifiers) stored by the database layer 1928, but not allowed access to other subject's individual medical information (with individual identifiers). Similarly, a subject's authorized healthcare provider or payor entity may be provided access to some or all of the subject's individual medical information (with individual identifiers) stored by the database layer 1928, but not allowed access to another individual's personal information. Also, an operator or administrator-user (on a separate computer communicating with the computing device 1900) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 1928 in the data storage devices 1929.

In exemplary embodiments, the database 1929 stores uploaded measurement data for a patient (e.g., sensor glucose measurement and characteristic impedance values) along with event log data consisting of event records created during a monitoring period corresponding to the measurement data. In embodiments of the invention, the database layer 1928 may also store preference profiles. In the database layer 1928, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 1929 in the database layer. Preference profiles may include various threshold values, monitoring period values, prioritization criteria, filtering criteria, and/or other user-specific values for parameters to generate a snapshot GUI display on the display 1933 or a support device 1912 in a personalized or patient-specific manner.

The DDMS 1916 may measure, analyze, and track either blood glucose (BG) or sensor glucose (SG) measurements (or readings) for a user. In embodiments of the invention, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 1930 may include a report wizard program that pulls data from selected locations in the database 1929 and generates report information from the desired parameters of interest. The reporting layer 1930 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar. In exemplary embodiments described herein, the reporting layer 1930 also facilitates generation of a snapshot report including a snapshot GUI display.

In embodiments of the invention, the database layer 1928 may calculate values for various medical information that is to be displayed on the reports generated by the report or reporting layer 1930. For example, the database layer 1928, may calculate average blood glucose or sensor glucose readings for specified timeframes. In embodiments of the invention, the reporting layer 1930 may calculate values for medical or physical information that is to be displayed on the reports. For example, a user may select parameters which are then utilized by the reporting layer 1930 to generate medical information values corresponding to the selected parameters. In other embodiments of the invention, the user may select a parameter profile that previously existed in the database layer 1928.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs. In this manner, users may import data from the system 1916 into further reporting tools familiar to the user. The reporting layer 1930 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 1930 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 1916 may allow a user generating a report to designate the report as non-printable and/or non-transferable, whereby the system 1916 will provide the report in a form that inhibits printing and/or electronic transfer.

The reporting layer 1930 may transfer selected reports to the graph display layer 1931. The graph display layer 1931 receives information regarding the selected reports and converts the data into a format that can be displayed or shown on a display 1933.

In embodiments of the invention, the reporting layer 1930 may store a number of the user's parameters. Illustratively, the reporting layer 1930 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well-being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well-being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 1932 supports interactions with the end user, for example, for user login and data access, software navigation, data input, user selection of desired report types and the display of selected information. Users may also input parameters to be utilized in the selected reports via the user interface layer 1932. Examples of users include but are not limited to: healthcare providers, healthcare payer entities, system operators or administrators, researchers, business entities, healthcare institutions and organizations, or the like, depending upon the service being provided by the system and depending upon the invention embodiment. More comprehensive embodiments are capable of interacting with some or all of the above-noted types of users, wherein different types of users have access to different services or data or different levels of services or data.

In an example embodiment, the user interface layer 1932 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 1916, depending upon the embodiment of use.

In another example embodiment, where the DDMS 1916 is located on one computing device 1900, the user interface layer 1932 provides a number of menus to the user to navigate through the DDMS. These menus may be created utilizing any menu format, including but not limited to HTML, XML, or Active Server pages. A user may access the DDMS 1916 to perform one or more of a variety of tasks, such as accessing general information made available on a website to all subjects or groups of subjects. The user interface layer 1932 of the DDMS 1916 may allow a user to access specific information or to generate reports regarding that subject's medical condition or that subject's medical device(s) 1912, to transfer data or other information from that subject's support device(s) 1912 to the system 1916, to transfer data, programs, program updates or other information from the system 1916 to the subject's support device(s) 1912, to manually enter information into the system 1916, to engage in a remote consultation exchange with a healthcare provider, or to modify the custom settings in a subject's supported device and/or in a subject's DDMS/MDMS data file.

The system 1916 may provide access to different optional resources or activities (including accessing different information items and services) to different users and to different types or groups of users, such that each user may have a customized experience and/or each type or group of user (e.g., all users, diabetic users, cardio users, healthcare provider-user or payor-user, or the like) may have a different set of information items or services available on the system. The system 1916 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 1916, based on the type of user and/or the identity of the user.

Upon entering successful verification of the user's identification information and password, the user may be provided access to secure, personalized information stored on the DDMS 1916. For example, the user may be provided access to a secure, personalized location in the DDMS 1916 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 1912 to the system 1916, manually enter additional data into the system 1916, modify the subject's custom settings, and/or view and print reports. Reports may include data specific to the subject's condition, including but not limited to, data obtained from the subject's subject support device(s) 1912, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 1929) employed by the database layer 1928.

The user may select an option to transfer (send) device data to the medical data management system 1916. If the system 1916 receives a user's request to transfer device data to the system, the system 1916 may provide the user with step-by-step instructions on how to transfer data from the subject's supported device(s) 1912. For example, the DDMS 1916 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 1912 used by the subject. The system 1916 employs that information to select the stored instruction set(s) associated with the particular subject's support device(s) 1912 for display to the user.

Other activities or resources available to the user on the system 1916 may include an option for manually entering information to the DDMS/MDMS 1916. For example, from the user's personalized menu or location, the user may select an option to manually enter additional information into the system 1916.

Further optional activities or resources may be available to the user on the DDMS 1916. For example, from the user's personalized menu, the user may select an option to receive data, software, software updates, treatment recommendations or other information from the system 1916 on the subject's support device(s) 1912. If the system 1916 receives a request from a user to receive data, software, software updates, treatment recommendations or other information, the system 1916 may provide the user with a list or other arrangement of multiple selectable icons or other indicia representing available data, software, software updates or other information available to the user.

Yet further optional activities or resources may be available to the user on the medical data management system 1916 including, for example, an option for the user to customize or otherwise further personalize the user's personalized location or menu. In particular, from the user's personalized location, the user may select an option to customize parameters for the user. In addition, the user may create profiles of customizable parameters. When the system 1916 receives such a request from a user, the system 1916 may provide the user with a list or other arrangement of multiple selectable icons or other indicia representing parameters that may be modified to accommodate the user's preferences. When a user selects one or more of the icons or other indicia, the system 1916 may receive the user's request and makes the requested modification.

In one or more exemplary embodiments, for an individual patient in the DDMS, the computing device 1900 of the DDMS is configured to analyze that patient's historical measurement data, historical delivery data, historical event log data, and any other historical or contextual data associated with the patient maintained in the database layer 1928 to support one or more of the processes of FIGS. 9-18. In this regard, machine learning, artificial intelligence, or similar mathematical modeling of the patient's physiological behavior or response may be performed at the computing device 1900 to facilitate patient-specific correlations or predictions. Current measurement data, delivery data, and event log data associated with the patient along with current contextual data may be analyzed using the resultant models, either at the computing device 1900 of the DDMS or another device 1912 to determine probable events, behaviors, or responses by the patient in real-time and generate appropriate recommendations, GUI displays, and the like in the manner described above. As a result, patient outcomes may be improved while reducing the burden on the patient to perform such patient-specific analysis or adjustments.

For the sake of brevity, conventional techniques related to glucose sensing and/or monitoring, sensor calibration and/or compensation, bolusing, machine learning and/or artificial intelligence, pharmodynamic modeling, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A system comprising:
    one or more processors; and
    one or more processor-readable media storing instructions which, when executed by the one or more processors, cause performance of:
        obtaining, from a medical device, measurement data for a patient,
        forecasting a plurality of values for a condition of the patient based on a forecasting model associated with the patient and the obtained measurement data for the patient,
        providing, for display on a portable electronic device, a graphical user interface depicting the plurality of forecasted values and comprising a plurality of adjustable graphical user interface elements, each adjustable graphical user interface element being associated with a time period and an activity or event likely to influence the condition of the patient,
        obtaining, via the graphical user interface, an adjustment to a first adjustable graphical user interface element of the graphical user interface,
        in response to obtaining the adjustment to the first adjustable graphical user interface element, updating at least one of the forecasted values for the condition of the patient based on the adjustment to the first adjustable graphical user interface element, the obtained measurement data, and the forecasting model associated with the patient, and
        dynamically updating the graphical user interface to reflect the updated at least one forecasted value.

2. The system of claim 1, wherein the measurement data is obtained from a glucose sensor device configured to monitor an interstitial glucose level of the patient.

3. The system of claim 1, wherein the activity or event associated with the first adjustable graphical user interface element of the graphical user interface is a meal event.

4. The system of claim 3, wherein the first adjustable graphical user interface element of the graphical user interface corresponds to an amount of carbohydrates associated with the meal event.

5. The system of claim 1, wherein the activity or event associated with the first adjustable graphical user interface element of the graphical user interface is a bolus event.

6. The system of claim 5, wherein the first adjustable graphical user interface element of the graphical user interface corresponds to an amount of insulin associated with the bolus event.

7. The system of claim 6, wherein the one or more processor-readable media further store instructions which, when executed by the one or more processors, cause performance of:
during the time period associated with the first adjustable graphical user interface element of the graphical user interface, causing delivery, by a fluid delivery device associated with the patient, of the amount of insulin associated with the bolus event.

8. The system of claim 1, wherein each of the forecasted values is a forecasted glucose level of the patient, wherein the one or more processor-readable media further store instructions which, when executed by the one or more processors, cause performance of:
after determining that a current glucose level during a particular time period deviates from a forecasted glucose level for the particular time period, providing a notification to the patient of the deviation.

9. A processor implemented method comprising:
obtaining, from a medical device, measurement data for a patient,
forecasting a plurality of values for a condition of the patient based on a forecasting model associated with the patient and the obtained measurement data for the patient,
providing, for display on a portable electronic device, a graphical user interface depicting the plurality of forecasted values and comprising a plurality of adjustable graphical user interface elements, each adjustable graphical user interface element being associated with a time period and an activity or event likely to influence the condition of the patient,
obtaining, via the graphical user interface, an adjustment to a first adjustable graphical user interface element of the graphical user interface,
in response to obtaining the adjustment to the first adjustable graphical user interface element, updating at least one of the forecasted values for the condition of the patient based on the adjustment to the first adjustable graphical user interface element, the obtained measurement data, and the forecasting model associated with the patient, and
dynamically updating the graphical user interface to reflect the updated at least one forecasted value.

10. The method of claim 9, wherein the measurement data is obtained from a glucose sensor device configured to monitor an interstitial glucose level of the patient.

11. The method of claim 9, wherein the activity or event associated with the first adjustable graphical user interface element of the graphical user interface is a meal event.

12. The method of claim 11, wherein the first adjustable graphical user interface element of the graphical user interface corresponds to an amount of carbohydrates associated with the meal event.

13. The method of claim 9, wherein the activity or event associated with the first adjustable graphical user interface element of the graphical user interface is a bolus event.

14. The method of claim 13, wherein the first adjustable graphical user interface element of the graphical user interface corresponds to an amount of insulin associated with the bolus event.

15. The method of claim 14, further comprising:
during the time period associated with the first adjustable graphical user interface element of the graphical user interface, causing delivery, by a fluid delivery device associated with the patient, of the amount of insulin associated with the bolus event.

16. The method of claim 9, wherein each of the forecasted values is a forecasted glucose level of the patient, the method further comprising:
after determining that a current glucose level during a particular time period deviates from a forecasted glucose level for the particular time period, providing a notification to the patient of the deviation.

17. One or more non-transitory processor-readable media storing instructions which, when executed by one or more processors, cause performance of:
obtaining, from a medical device, measurement data for a patient,
forecasting a plurality of values for a condition of the patient based on a forecasting model associated with the patient and the obtained measurement data for the patient,
providing, for display on a portable electronic device, a graphical user interface depicting the plurality of forecasted values and comprising a plurality of adjustable graphical user interface elements, each adjustable graphical user interface element being associated with a time period and an activity or event likely to influence the condition of the patient,
obtaining, via the graphical user interface, an adjustment to a first adjustable graphical user interface element of the graphical user interface,
in response to obtaining the adjustment to the first adjustable graphical user interface element, updating at least one of the forecasted values for the condition of the patient based on the adjustment to the first adjustable graphical user interface element, the obtained measurement data, and the forecasting model associated with the patient, and
dynamically updating the graphical user interface to reflect the updated at least one forecasted value.

18. The one or more non-transitory processor-readable media of claim 17, wherein the measurement data is obtained from a glucose sensor device configured to monitor an interstitial glucose level of the patient.

19. The one or more non-transitory processor-readable media of claim 17, wherein the activity or event associated with the first adjustable graphical user interface element of the graphical user interface is a meal event.

20. The one or more non-transitory processor-readable media of claim 19, wherein the first adjustable graphical user interface element of the graphical user interface corresponds to an amount of carbohydrates associated with the meal event.

* * * * *